(12) United States Patent
Al-Ali et al.

(10) Patent No.: US 12,744,134 B2
(45) **Date of Patent: *Sep. 22, 2026**

(54) AUTOMATED ASSEMBLY SENSOR CABLE

(71) Applicant: MASIMO CORPORATION, Irvine, CA (US)

(72) Inventors: Ammar Al-Ali, San Juan Capistrano, CA (US); Yassir Abdul-Hafiz, Irvine, CA (US); William Jack MacNeish, III, Newport Beach, CA (US); Kevin Forrest, Rancho Santa Margarita, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/084,257

(22) Filed: Dec. 19, 2022

(65) Prior Publication Data

US 2023/0230726 A1 Jul. 20, 2023

Related U.S. Application Data

(63) Continuation of application No. 17/354,117, filed on Jun. 22, 2021, now Pat. No. 11,557,407, which is a (Continued)

(51) Int. Cl.
*H01B 9/02* (2006.01)
*A61B 5/1455* (2006.01)

(Continued)

(52) U.S. Cl.
CPC ......... *H01B 9/028* (2013.01); *A61B 5/14552* (2013.01); *H01B 7/0823* (2013.01);

(Continued)

(58) Field of Classification Search
CPC ........ H01B 9/02; H01B 9/028; H01B 7/0823; H01B 7/08

(Continued)

(56) References Cited

U.S. PATENT DOCUMENTS 2,628,998 A * 2/1953 Frisbie ................ H01B 7/0823 425/114
4,221,756 A * 9/1980 Piper ................... H01B 13/144 425/114

(Continued)

FOREIGN PATENT DOCUMENTS

WO WO 92/010842 6/1992
WO WO 03/058646 7/2003

OTHER PUBLICATIONS

US 9,579,050 B2, 02/2017, Al-Ali (withdrawn)

(Continued)

*Primary Examiner* — William H. Mayo, III
(74) *Attorney, Agent, or Firm* — Knobbe, Martens, Olson, & Bear, LLP

(57) ABSTRACT

An automated assembly sensor cable has a generally wide and flat elongated body and a registration feature generally traversing the length of the body so as to identify the relative locations of conductors within the body. This cable configuration facilitates the automated attachment of the cable to an optical sensor circuit and corresponding connector. In various embodiments, the automated assembly sensor cable has a conductor set of insulated wires, a conductive inner jacket generally surrounding the conductor set, an outer jacket generally surrounding the inner jacket and a registration feature disposed along the surface of the outer jacket and a conductive drain line is embedded within the inner jacket. A strength member may be embedded within the inner jacket.

17 Claims, 6 Drawing Sheets

Related U.S. Application Data continuation of application No. 15/637,835, filed on Jun. 29, 2017, now Pat. No. 11,069,461, which is a continuation of application No. 13/951,313, filed on Jul. 25, 2013, now Pat. No. 9,697,928.

(60) Provisional application No. 61/678,107, filed on Aug. 1, 2012.

(51) Int. Cl.
*H01B 7/08* (2006.01)
*H01B 7/36* (2006.01)

(52) U.S. Cl.
CPC ............. *H01B 7/36* (2013.01); *H01B 7/0861* (2013.01); *Y10T 29/49147* (2015.01); *Y10T 29/49149* (2015.01); *Y10T 29/49174* (2015.01)

(58) Field of Classification Search
USPC ............. 174/110 R, 102 R, 108, 109, 113 R, 174/117 F, 117 FF
See application file for complete search history.

(56) References Cited

U.S. PATENT DOCUMENTS 4,277,642 A * 7/1981 Piper .................... B29C 48/156 174/117 FF
4,308,421 A 12/1981 Bogese, II
4,425,475 A * 1/1984 Ward ...................... H01B 7/04 174/131 A
4,638,117 A * 1/1987 Ney ....................... H01B 7/38 174/115
4,761,053 A * 8/1988 Cogelia ............... G02B 6/4439 428/383
4,801,764 A * 1/1989 Ohlhaber ................ H01B 7/08 174/117 F
4,960,128 A 10/1990 Gordon et al.
4,964,408 A 10/1990 Hink et al.
5,041,187 A 8/1991 Hink et al.
5,069,213 A 12/1991 Hink et al.
5,132,489 A * 7/1992 Yamano .............. H01B 11/203 174/115
5,155,304 A * 10/1992 Gossett ................. H01B 7/183 385/113
5,163,438 A 11/1992 Gordon et al.
5,179,251 A * 1/1993 Mullin ................ G02B 6/4426 174/23 C
5,319,355 A 6/1994 Russek
5,337,744 A 8/1994 Branigan
5,341,805 A 8/1994 Stavridi et al.
D353,195 S 12/1994 Savage et al.
D353,196 S 12/1994 Savage et al.
5,377,676 A 1/1995 Vari et al.
D359,546 S 6/1995 Savage et al.
5,431,170 A 7/1995 Mathews
5,436,499 A 7/1995 Namavar et al.
D361,840 S 8/1995 Savage et al.
D362,063 S 9/1995 Savage et al.
5,452,717 A 9/1995 Branigan et al.
D363,120 S 10/1995 Savage et al.
5,456,252 A 10/1995 Vari et al.
5,479,934 A 1/1996 Imran
5,482,036 A 1/1996 Diab et al.
5,490,505 A 2/1996 Diab et al.
5,494,043 A 2/1996 O'Sullivan et al.
5,533,511 A 7/1996 Kaspari et al.
5,534,851 A 7/1996 Russek
5,561,275 A 10/1996 Savage et al.
5,590,649 A 1/1997 Caro et al.
5,602,924 A 2/1997 Durand et al.
5,632,272 A 5/1997 Diab et al.
5,638,816 A 6/1997 Kiani-Azarbayjany et al.
5,638,818 A 6/1997 Diab et al.
5,645,440 A 7/1997 Tobler et al.
5,671,914 A 9/1997 Kalkhoran et al.
5,685,299 A 11/1997 Diab et al.
5,704,189 A 1/1998 Collier
5,726,440 A 3/1998 Kalkhoran et al.
D393,830 S 4/1998 Tobler et al.
5,743,262 A 4/1998 Lepper, Jr. et al.
5,747,806 A 5/1998 Khalil et al.
5,750,994 A 5/1998 Schlager
5,758,644 A 6/1998 Diab et al.
5,760,910 A 6/1998 Lepper, Jr. et al.
5,769,785 A 6/1998 Diab et al.
5,782,757 A 7/1998 Diab et al.
5,785,659 A 7/1998 Caro et al.
5,791,347 A 8/1998 Flaherty et al.
5,810,734 A 9/1998 Caro et al.
5,823,950 A 10/1998 Diab et al.
5,830,131 A 11/1998 Caro et al.
5,833,618 A 11/1998 Caro et al.
5,860,919 A 1/1999 Kiani-Azarbayjany et al.
5,890,929 A 4/1999 Mills et al.
5,904,654 A 5/1999 Wohltmann et al.
5,919,134 A 7/1999 Diab
5,934,925 A 8/1999 Tobler et al.
5,940,182 A 8/1999 Lepper, Jr. et al.
5,973,268 A * 10/1999 Cheng ................... H01B 7/361 174/117 F
5,987,343 A 11/1999 Kinast
5,995,855 A 11/1999 Kiani et al.
5,997,343 A 12/1999 Mills et al.
6,002,952 A 12/1999 Diab et al.
6,010,937 A 1/2000 Karam et al.
6,011,986 A 1/2000 Diab et al.
6,027,452 A 2/2000 Flaherty et al.
6,036,642 A 3/2000 Diab et al.
6,040,578 A 3/2000 Malin et al.
6,045,509 A 4/2000 Caro et al.
6,066,204 A 5/2000 Haven
6,067,462 A 5/2000 Diab et al.
6,081,735 A 6/2000 Diab et al.
6,088,607 A 7/2000 Diab et al.
6,110,522 A 8/2000 Lepper, Jr. et al.
6,115,673 A 9/2000 Malin et al.
6,124,597 A 9/2000 Shehada et al.
6,128,521 A 10/2000 Marro et al.
6,129,675 A 10/2000 Jay
6,144,868 A 11/2000 Parker
6,151,516 A 11/2000 Kiani-Azarbayjany et al.
6,152,754 A 11/2000 Gerhardt et al.
6,157,850 A 12/2000 Diab et al.
6,165,005 A 12/2000 Mills et al.
6,184,521 B1 2/2001 Coffin, IV et al.
6,206,830 B1 3/2001 Diab et al.
6,229,856 B1 5/2001 Diab et al.
6,232,609 B1 5/2001 Snyder et al.
6,236,872 B1 5/2001 Diab et al.
6,241,683 B1 6/2001 Macklem et al.
6,253,097 B1 6/2001 Aronow et al.
6,255,708 B1 7/2001 Sudharsanan et al.
6,256,523 B1 7/2001 Diab et al.
6,263,222 B1 7/2001 Diab et al.
6,278,522 B1 8/2001 Lepper, Jr. et al.
6,280,213 B1 8/2001 Tobler et al.
6,280,381 B1 8/2001 Malin et al.
6,285,896 B1 9/2001 Tobler et al.
6,301,493 B1 10/2001 Marro et al.
6,308,089 B1 10/2001 von der Ruhr et al.
6,317,627 B1 11/2001 Ennen et al.
6,321,100 B1 11/2001 Parker
6,325,761 B1 12/2001 Jay
6,334,065 B1 12/2001 Al-Ali et al.
6,343,224 B1 1/2002 Parker
6,349,228 B1 2/2002 Kiani et al.
6,360,114 B1 3/2002 Diab et al.
6,368,283 B1 4/2002 Xu et al.
6,371,921 B1 4/2002 Caro et al.
6,377,829 B1 4/2002 Al-Ali
6,388,240 B2 5/2002 Schulz et al.
6,397,091 B2 5/2002 Diab et al.
6,411,373 B1 6/2002 Garside et al.

(56) References Cited

U.S. PATENT DOCUMENTS 6,415,167 B1 7/2002 Blank et al.
6,430,437 B1 8/2002 Marro
6,430,525 B1 8/2002 Weber et al.
6,463,311 B1 10/2002 Diab
6,470,199 B1 10/2002 Kopotic et al.
6,487,429 B2 11/2002 Hockersmith et al.
6,501,975 B2 12/2002 Diab et al.
6,505,059 B1 1/2003 Kollias et al.
6,509,526 B2 * 1/2003 Osornio ............... H01B 11/002 174/117 FF
6,515,273 B2 2/2003 Al-Ali
6,519,487 B1 2/2003 Parker
6,525,386 B1 2/2003 Mills et al.
6,526,300 B1 2/2003 Kiani et al.
6,534,012 B1 3/2003 Hazen et al.
6,541,756 B2 4/2003 Schulz et al.
6,542,764 B1 4/2003 Al-Ali et al.
6,580,086 B1 6/2003 Schulz et al.
6,584,336 B1 6/2003 Ali et al.
6,587,196 B1 7/2003 Stippick et al.
6,587,199 B1 7/2003 Luu
6,595,316 B2 7/2003 Cybulski et al.
6,597,932 B2 7/2003 Tian et al.
6,597,933 B2 7/2003 Kiani et al.
6,606,511 B1 8/2003 Ali et al.
6,632,181 B2 10/2003 Flaherty et al.
6,635,559 B2 10/2003 Greenwald et al.
6,639,668 B1 10/2003 Trepagnier
6,640,116 B2 10/2003 Diab
6,640,117 B2 10/2003 Makarewicz et al.
6,643,530 B2 11/2003 Diab et al.
6,650,917 B2 11/2003 Diab et al.
6,654,624 B2 11/2003 Diab et al.
6,658,276 B2 12/2003 Kiani et al.
6,661,161 B1 12/2003 Lanzo et al.
6,671,531 B2 12/2003 Al-Ali
6,678,543 B2 1/2004 Diab et al.
6,684,090 B2 1/2004 Ali et al.
6,684,091 B2 1/2004 Parker
6,697,656 B1 2/2004 Al-Ali
6,697,657 B1 2/2004 Shehada et al.
6,697,658 B2 2/2004 Al-Ali
RE38,476 E 3/2004 Diab et al.
6,699,194 B1 3/2004 Diab et al.
6,714,804 B2 3/2004 Al-Ali et al.
RE38,492 E 4/2004 Diab et al.
6,721,582 B2 4/2004 Trepagnier et al.
6,721,585 B1 4/2004 Parker
6,725,075 B2 4/2004 Al-Ali
6,728,560 B2 4/2004 Kollias et al.
6,734,362 B2 * 5/2004 Buck ..................... H01B 7/041 174/117 F
6,735,459 B2 5/2004 Parker
6,738,652 B2 5/2004 Mattu et al.
6,745,060 B2 6/2004 Diab et al.
6,760,607 B2 * 7/2004 Ai-All ................ A61B 5/14552 600/322
6,770,028 B1 8/2004 Ali et al.
6,771,994 B2 8/2004 Kiani et al.
6,788,965 B2 9/2004 Ruchti et al.
6,792,300 B1 9/2004 Diab et al.
6,813,511 B2 11/2004 Diab et al.
6,816,241 B2 11/2004 Grubisic
6,816,741 B2 11/2004 Diab
6,822,564 B2 11/2004 Ai-Ai
6,826,419 B2 11/2004 Diab et al.
6,830,711 B2 12/2004 Mills et al.
6,850,787 B2 2/2005 Weber et al.
6,850,788 B2 2/2005 Al-Ali
6,852,083 B2 2/2005 Caro et al.
6,861,639 B2 3/2005 Al-Ali
6,876,931 B2 4/2005 Lorenz et al.
6,898,452 B2 5/2005 Al-Ali et al.
6,920,345 B2 7/2005 Al-Ali et al.
6,931,268 B1 8/2005 Kiani-Azarbayjany et al.
6,934,570 B2 8/2005 Kiani et al.
6,939,305 B2 9/2005 Flaherty et al.
6,943,348 B1 9/2005 Coffin, IV
6,950,687 B2 9/2005 Al-Ali
6,956,649 B2 10/2005 Acosta et al.
6,961,598 B2 11/2005 Diab
6,970,792 B1 11/2005 Diab
6,979,812 B2 12/2005 Ai-Ai
6,985,764 B2 1/2006 Mason et al.
6,990,364 B2 1/2006 Ruchti et al.
6,993,371 B2 1/2006 Kiani et al.
6,996,427 B2 2/2006 Ali et al.
6,998,247 B2 2/2006 Monfre et al.
6,999,904 B2 2/2006 Weber et al.
7,003,338 B2 2/2006 Weber et al.
7,003,339 B2 2/2006 Diab et al.
7,015,451 B2 3/2006 Dalke et al.
7,024,233 B2 4/2006 Ali et al.
7,027,849 B2 4/2006 Al-Ali
7,030,749 B2 4/2006 Al-Ali
7,039,449 B2 5/2006 Al-Ali
7,041,060 B2 5/2006 Flaherty et al.
7,044,918 B2 5/2006 Diab
7,067,893 B2 6/2006 Mills et al.
D526,719 S 8/2006 Richie, Jr. et al.
7,096,052 B2 8/2006 Mason et al.
7,096,054 B2 8/2006 Abdul-Hafiz et al.
D529,616 S 10/2006 Deros et al.
7,132,641 B2 11/2006 Schulz et al.
7,133,710 B2 11/2006 Acosta et al.
7,142,901 B2 11/2006 Kiani et al.
7,149,561 B2 12/2006 Diab
7,186,966 B2 3/2007 Al-Ali
7,190,261 B2 3/2007 Al-Ali
7,215,984 B2 5/2007 Diab et al.
7,215,986 B2 5/2007 Diab et al.
7,221,971 B2 5/2007 Diab et al.
7,225,006 B2 5/2007 Al-Ali et al.
7,225,007 B2 5/2007 Al-Ali et al.
RE39,672 E 6/2007 Shehada et al.
7,239,905 B2 7/2007 Kiani-Azarbayjany et al.
7,245,953 B1 7/2007 Parker
7,254,429 B2 8/2007 Schurman et al.
7,254,431 B2 8/2007 Al-Ali et al.
7,254,433 B2 8/2007 Diab et al.
7,254,434 B2 8/2007 Schulz et al.
7,272,425 B2 9/2007 Al-Ali
7,274,955 B2 9/2007 Kiani et al.
D554,263 S 10/2007 Al-Ali et al.
7,280,858 B2 10/2007 Al-Ali et al.
7,289,835 B2 10/2007 Mansfield et al.
7,292,883 B2 11/2007 De Felice et al.
7,295,866 B2 11/2007 Al-Ali
7,328,053 B1 2/2008 Diab et al.
7,332,784 B2 2/2008 Mills et al.
7,340,287 B2 3/2008 Mason et al.
7,341,559 B2 3/2008 Schulz et al.
7,343,186 B2 3/2008 Lamego et al.
D566,282 S 4/2008 Al-Ali et al.
7,355,512 B1 4/2008 Al-Ali
7,356,365 B2 4/2008 Schurman
7,371,981 B2 5/2008 Abdul-Hafiz
7,373,193 B2 5/2008 Al-Ali et al.
7,373,194 B2 5/2008 Weber et al.
7,376,453 B1 5/2008 Diab et al.
7,377,794 B2 5/2008 Al-Ali et al.
7,377,899 B2 5/2008 Weber et al.
7,383,070 B2 6/2008 Diab et al.
7,395,158 B2 7/2008 Monfre et al.
7,415,297 B2 8/2008 Al-Ali et al.
7,428,432 B2 9/2008 Ali et al.
7,438,683 B2 10/2008 Al-Ali et al.
7,440,787 B2 10/2008 Diab
7,454,240 B2 11/2008 Diab et al.
7,467,002 B2 12/2008 Weber et al.
7,469,157 B2 12/2008 Diab et al.
7,471,969 B2 12/2008 Diab et al.
7,471,971 B2 12/2008 Diab et al.
7,483,729 B2 1/2009 Al-Ali et al.

(56) References Cited

U.S. PATENT DOCUMENTS 7,483,730 B2 1/2009 Diab et al.
7,489,958 B2 2/2009 Diab et al.
7,496,391 B2 2/2009 Diab et al.
7,496,393 B2 2/2009 Diab et al.
D587,657 S 3/2009 Al-Ali et al.
7,499,741 B2 3/2009 Diab et al.
7,499,835 B2 3/2009 Weber et al.
7,500,950 B2 3/2009 Al-Ali et al.
7,509,154 B2 3/2009 Diab et al.
7,509,494 B2 3/2009 Al-Ali
7,510,849 B2 3/2009 Schurman et al.
7,514,725 B2 4/2009 Wojtczuk et al.
7,519,406 B2 4/2009 Blank et al.
7,526,328 B2 4/2009 Diab et al.
D592,507 S 5/2009 Wachman et al.
7,530,942 B1 5/2009 Diab
7,530,949 B2 5/2009 Al Ali et al.
7,530,955 B2 5/2009 Diab et al.
7,563,110 B2 7/2009 Al-Ali et al.
7,593,230 B2 9/2009 Abul-Haj et al.
7,596,398 B2 9/2009 Al-Ali et al.
7,606,608 B2 10/2009 Blank et al.
7,618,375 B2 11/2009 Flaherty et al.
7,620,674 B2 11/2009 Ruchti et al.
D606,659 S 12/2009 Kiani et al.
7,629,039 B2 12/2009 Eckerbom et al.
7,640,140 B2 12/2009 Ruchti et al.
7,647,083 B2 1/2010 Al-Ali et al.
D609,193 S 2/2010 Al-Ali et al.
D614,305 S 4/2010 Al-Ali et al.
7,697,966 B2 4/2010 Monfre et al.
7,698,105 B2 4/2010 Ruchti et al.
RE41,317 E 5/2010 Parker
RE41,333 E 5/2010 Blank et al.
7,729,733 B2 6/2010 Al-Ali et al.
7,734,320 B2 6/2010 Al-Ali
7,761,127 B2 7/2010 Al-Ali et al.
7,761,128 B2 7/2010 Al-Ali et al.
7,764,982 B2 7/2010 Dalke et al.
D621,516 S 8/2010 Kiani et al.
7,791,155 B2 9/2010 Diab
7,801,581 B2 9/2010 Diab
7,822,452 B2 10/2010 Schurman et al.
RE41,912 E 11/2010 Parker
7,844,313 B2 11/2010 Kiani et al.
7,844,314 B2 11/2010 Al-Ali
7,844,315 B2 11/2010 Al-Ali
7,865,222 B2 1/2011 Weber et al.
7,873,497 B2 1/2011 Weber et al.
7,880,606 B2 2/2011 Ai-Ai
7,880,626 B2 2/2011 Al-Ali et al.
7,891,355 B2 2/2011 Al-Ali et al.
7,894,868 B2 2/2011 Al-Ali et al.
7,899,507 B2 3/2011 Al-Ali et al.
7,904,132 B2 3/2011 Weber et al.
7,909,772 B2 3/2011 Popov et al.
7,910,875 B2 3/2011 Al-Ali
7,919,713 B2 4/2011 Al-Ali et al.
7,937,128 B2 5/2011 Al-Ali
7,937,129 B2 5/2011 Mason et al.
7,937,130 B2 5/2011 Diab et al.
7,941,199 B2 5/2011 Kiani
7,951,086 B2 5/2011 Flaherty et al.
7,957,780 B2 6/2011 Lamego et al.
7,962,188 B2 6/2011 Kiani et al.
7,962,190 B1 6/2011 Diab et al.
7,976,472 B2 7/2011 Kiani
7,988,637 B2 8/2011 Diab
7,990,382 B2 8/2011 Kiani
7,991,446 B2 8/2011 Ali et al.
8,000,761 B2 8/2011 Al-Ali
8,008,088 B2 8/2011 Bellott et al.
RE42,753 E 9/2011 Kiani-Azarbayjany et al.
8,019,400 B2 9/2011 Diab et al.
8,028,701 B2 10/2011 Al-Ali et al.
8,029,765 B2 10/2011 Bellott et al.
8,036,727 B2 10/2011 Schurman et al.
8,036,728 B2 10/2011 Diab et al.
8,046,040 B2 10/2011 Ali et al.
8,046,041 B2 10/2011 Diab et al.
8,046,042 B2 10/2011 Diab et al.
8,048,040 B2 11/2011 Kiani
8,050,728 B2 11/2011 Al-Ali et al.
RE43,169 E 2/2012 Parker
8,118,620 B2 2/2012 Al-Ali et al.
8,126,528 B2 2/2012 Diab et al.
8,128,572 B2 3/2012 Diab et al.
8,130,105 B2 3/2012 Al-Ali et al.
8,145,287 B2 3/2012 Diab et al.
8,150,487 B2 4/2012 Diab et al.
8,175,672 B2 5/2012 Parker
8,180,420 B2 5/2012 Diab et al.
8,182,443 B1 5/2012 Kiani
8,185,180 B2 5/2012 Diab et al.
8,190,223 B2 5/2012 Al-Ali et al.
8,190,227 B2 5/2012 Diab et al.
8,203,438 B2 6/2012 Kiani et al.
8,203,704 B2 6/2012 Merritt et al.
8,204,566 B2 6/2012 Schurman et al.
8,219,172 B2 7/2012 Schurman et al.
8,224,411 B2 7/2012 Al-Ali et al.
8,228,181 B2 7/2012 Al-Ali
8,229,532 B2 7/2012 Davis
8,229,533 B2 7/2012 Diab et al.
8,233,955 B2 7/2012 Al-Ali et al.
8,244,325 B2 8/2012 Al-Ali et al.
8,255,026 B1 8/2012 Al-Ali
8,255,027 B2 8/2012 Al-Ali et al.
8,255,028 B2 8/2012 Al-Ali et al.
8,260,577 B2 9/2012 Weber et al.
8,265,723 B1 9/2012 McHale et al.
8,274,360 B2 9/2012 Sampath et al.
8,280,473 B2 10/2012 Al-Ali
8,301,217 B2 10/2012 Al-Ali et al.
8,306,596 B2 11/2012 Schurman et al.
8,310,336 B2 11/2012 Muhsin et al.
8,315,683 B2 11/2012 Al-Ali et al.
RE43,860 E 12/2012 Parker
8,337,403 B2 12/2012 Al-Ali et al.
8,346,330 B2 1/2013 Lamego
8,353,842 B2 1/2013 Al-Ali et al.
8,355,766 B2 1/2013 MacNeish, III et al.
8,359,080 B2 1/2013 Diab et al.
8,364,223 B2 1/2013 Al-Ali et al.
8,364,226 B2 1/2013 Diab et al.
8,374,665 B2 2/2013 Lamego
8,385,995 B2 2/2013 Al-Ali et al.
8,385,996 B2 2/2013 Smith et al.
8,388,353 B2 3/2013 Kiani et al.
8,399,822 B2 3/2013 Ai-Ali
8,401,602 B2 3/2013 Kiani
8,405,608 B2 3/2013 Al-Ali et al.
8,414,499 B2 4/2013 Al-Ali et al.
8,418,524 B2 4/2013 Al-Ali
8,423,106 B2 4/2013 Lamego et al.
8,428,967 B2 4/2013 Olsen et al.
8,430,817 B1 4/2013 Al-Ali et al.
8,437,825 B2 5/2013 Dalvi et al.
8,455,290 B2 6/2013 Siskavich
8,457,703 B2 6/2013 Al-Ali
8,457,707 B2 6/2013 Kiani
8,463,349 B2 6/2013 Diab et al.
8,466,286 B2 6/2013 Bellott et al.
8,471,713 B2 6/2013 Poeze et al.
8,473,020 B2 6/2013 Kiani et al.
8,483,787 B2 7/2013 Al-Ali et al.
8,489,364 B2 7/2013 Weber et al.
8,498,684 B2 7/2013 Weber et al.
8,504,128 B2 8/2013 Blank et al.
8,509,867 B2 8/2013 Workman et al.
8,515,509 B2 8/2013 Bruinsma et al.
8,523,781 B2 9/2013 Al-Ali
8,529,301 B2 9/2013 Al-Ali et al.
8,532,727 B2 9/2013 Ali et al.

(56) References Cited

U.S. PATENT DOCUMENTS 8,532,728 B2 9/2013 Diab et al.
D692,145 S 10/2013 Al-Ali et al.
8,547,209 B2 10/2013 Kiani et al.
8,548,548 B2 10/2013 Al-Ali
8,548,549 B2 10/2013 Schurman et al.
8,548,550 B2 10/2013 Al-Ali et al.
8,560,032 B2 10/2013 Al-Ali et al.
8,560,034 B1 10/2013 Diab et al.
8,570,167 B2 10/2013 Al-Ali
8,570,503 B2 10/2013 Vo et al.
8,571,617 B2 10/2013 Reichgott et al.
8,571,618 B1 10/2013 Lamego et al.
8,571,619 B2 10/2013 Al-Ali et al.
8,577,431 B2 11/2013 Lamego et al.
8,581,732 B2 11/2013 Al-Ali et al.
8,584,345 B2 11/2013 Al-Ali et al.
8,588,880 B2 11/2013 Abdul-Hafiz et al.
8,600,467 B2 12/2013 Al-Ali et al.
8,606,342 B2 12/2013 Diab
8,626,255 B2 1/2014 Al-Ali et al.
8,630,691 B2 1/2014 Lamego et al.
8,634,889 B2 1/2014 Al-Ali et al.
8,641,631 B2 2/2014 Sierra et al.
8,652,060 B2 2/2014 Al-Ali
8,663,107 B2 3/2014 Kiani
8,666,468 B1 3/2014 Al-Ali
8,667,967 B2 3/2014 Al-Ali et al.
8,670,811 B2 3/2014 O'Reilly
8,670,814 B2 3/2014 Diab et al.
8,676,286 B2 3/2014 Weber et al.
8,682,407 B2 3/2014 Al-Ali
RE44,823 E 4/2014 Parker
RE44,875 E 4/2014 Kiani et al.
8,688,183 B2 4/2014 Bruinsma et al.
8,690,799 B2 4/2014 Telfort et al.
8,700,112 B2 4/2014 Kiani
8,702,627 B2 4/2014 Telfort et al.
8,706,179 B2 4/2014 Parker
8,712,494 B1 4/2014 MacNeish, III et al.
8,715,206 B2 5/2014 Telfort et al.
8,718,735 B2 5/2014 Lamego et al.
8,718,737 B2 5/2014 Diab et al.
8,718,738 B2 5/2014 Blank et al.
8,720,249 B2 5/2014 Al-Ali
8,721,541 B2 5/2014 Al-Ali et al.
8,721,542 B2 5/2014 Al-Ali et al.
8,723,677 B1 5/2014 Kiani
8,740,792 B1 6/2014 Kiani et al.
8,754,776 B2 6/2014 Poeze et al.
8,755,535 B2 6/2014 Telfort et al.
8,755,856 B2 6/2014 Diab et al.
8,755,872 B1 6/2014 Marinow
8,761,850 B2 6/2014 Lamego
8,764,671 B2 7/2014 Kiani
8,768,423 B2 7/2014 Shakespeare et al.
8,771,204 B2 7/2014 Telfort et al.
8,777,634 B2 7/2014 Kiani et al.
8,781,543 B2 7/2014 Diab et al.
8,781,544 B2 7/2014 Al-Ali et al.
8,781,549 B2 7/2014 Al-Ali et al.
8,788,003 B2 7/2014 Schurman et al.
8,790,268 B2 7/2014 Ai-Ali
8,801,613 B2 8/2014 Al-Ali et al.
8,821,397 B2 9/2014 Al-Ali et al.
8,821,415 B2 9/2014 Al-Ali et al.
8,830,449 B1 9/2014 Lamego et al.
8,831,700 B2 9/2014 Schurman et al.
8,840,549 B2 9/2014 Al-Ali et al.
8,847,740 B2 9/2014 Kiani et al.
8,849,365 B2 9/2014 Smith et al.
8,852,094 B2 10/2014 Al-Ali et al.
8,852,994 B2 10/2014 Wojtczuk et al.
8,868,147 B2 10/2014 Stippick et al.
8,868,150 B2 10/2014 Al-Ali et al.
8,870,792 B2 10/2014 Al-Ali et al.
8,886,271 B2 11/2014 Kiani et al.
8,888,539 B2 11/2014 Al-Ali et al.
8,888,708 B2 11/2014 Diab et al.
8,892,180 B2 11/2014 Weber et al.
8,897,847 B2 11/2014 Al-Ali
8,909,310 B2 12/2014 Lamego et al.
8,911,377 B2 12/2014 Al-Ali
8,912,909 B2 12/2014 Al-Ali et al.
8,920,317 B2 12/2014 Al-Ali et al.
8,921,699 B2 12/2014 Al-Ali et al.
8,922,382 B2 12/2014 Al-Ali et al.
8,929,964 B2 1/2015 Al-Ali et al.
8,942,777 B2 1/2015 Diab et al.
8,948,834 B2 2/2015 Diab et al.
8,948,835 B2 2/2015 Diab
8,965,471 B2 2/2015 Lamego
8,983,564 B2 3/2015 Al-Ali
8,989,831 B2 3/2015 Al-Ali et al.
8,996,085 B2 3/2015 Kiani et al.
8,998,809 B2 4/2015 Kiani
9,028,429 B2 5/2015 Telfort et al.
9,037,207 B2 5/2015 Al-Ali et al.
9,060,721 B2 6/2015 Reichgott et al.
9,066,666 B2 6/2015 Kiani
9,066,680 B1 6/2015 Al-Ali et al.
9,072,474 B2 7/2015 Al-Ali et al.
9,078,560 B2 7/2015 Schurman et al.
9,084,569 B2 7/2015 Weber et al.
9,095,316 B2 8/2015 Welch et al.
9,106,038 B2 8/2015 Telfort et al.
9,107,625 B2 8/2015 Telfort et al.
9,107,626 B2 8/2015 Al-Ali et al.
9,113,831 B2 8/2015 Al-Ali
9,113,832 B2 8/2015 Al-Ali
9,119,595 B2 9/2015 Lamego
9,131,881 B2 9/2015 Diab et al.
9,131,882 B2 9/2015 Al-Ali et al.
9,131,883 B2 9/2015 Al-Ali
9,131,917 B2 9/2015 Telfort et al.
9,138,180 B1 9/2015 Coverston et al.
9,138,182 B2 9/2015 Al-Ali et al.
9,138,192 B2 9/2015 Weber et al.
9,142,117 B2 9/2015 Muhsin et al.
9,153,112 B1 10/2015 Kiani et al.
9,153,121 B2 10/2015 Kiani et al.
9,161,696 B2 10/2015 Al-Ali et al.
9,161,713 B2 10/2015 Al-Ali et al.
9,167,995 B2 10/2015 Lamego et al.
9,176,141 B2 11/2015 Al-Ali et al.
9,186,102 B2 11/2015 Bruinsma et al.
9,192,312 B2 11/2015 Al-Ali
9,192,329 B2 11/2015 Al-Ali
9,192,351 B1 11/2015 Telfort et al.
9,195,385 B2 11/2015 Al-Ali et al.
9,211,072 B2 12/2015 Kiani
9,211,095 B1 12/2015 Al-Ali
9,218,454 B2 12/2015 Kiani et al.
9,226,696 B2 1/2016 Kiani
9,241,662 B2 1/2016 Al-Ali et al.
9,245,668 B1 1/2016 Vo et al.
9,259,185 B2 2/2016 Abdul-Hafiz et al.
9,267,572 B2 2/2016 Barker et al.
9,277,880 B2 3/2016 Poeze et al.
9,289,167 B2 3/2016 Diab et al.
9,295,421 B2 3/2016 Kiani et al.
9,307,928 B1 4/2016 Al-Ali et al.
9,323,894 B2 4/2016 Kiani
D755,392 S 5/2016 Hwang et al.
9,326,712 B1 5/2016 Kiani
9,333,316 B2 5/2016 Kiani
9,339,220 B2 5/2016 Lamego et al.
9,341,565 B2 5/2016 Lamego et al.
9,351,673 B2 5/2016 Diab et al.
9,351,675 B2 5/2016 Al-Ali et al.
9,364,181 B2 6/2016 Kiani et al.
9,368,671 B2 6/2016 Wojtczuk et al.
9,370,325 B2 6/2016 Al-Ali et al.
9,370,326 B2 6/2016 McHale et al.
9,370,335 B2 6/2016 Al-Ali et al.

(56) References Cited

U.S. PATENT DOCUMENTS 9,375,185 B2 6/2016 Ali et al.
9,386,953 B2 7/2016 Al-Ali
9,386,961 B2 7/2016 Al-Ali et al.
9,392,945 B2 7/2016 Al-Ali et al.
9,397,448 B2 7/2016 Al-Ali et al.
9,408,542 B1 8/2016 Kinast et al.
9,436,645 B2 9/2016 Al-Ali et al.
9,445,759 B1 9/2016 Lamego et al.
9,466,919 B2 10/2016 Kiani et al.
9,474,474 B2 10/2016 Lamego et al.
9,480,422 B2 11/2016 Al-Ali
9,480,435 B2 11/2016 Olsen
9,492,110 B2 11/2016 Al-Ali et al.
9,510,779 B2 12/2016 Poeze et al.
9,517,024 B2 12/2016 Kiani et al.
9,532,722 B2 1/2017 Lamego et al.
9,538,949 B2 1/2017 Al-Ali et al.
9,538,980 B2 1/2017 Telfort et al.
9,549,696 B2 1/2017 Lamego et al.
9,554,737 B2 1/2017 Schurman et al.
9,560,996 B2 2/2017 Kiani
9,560,998 B2 2/2017 Al-Ali et al.
9,566,019 B2 2/2017 Al-Ali et al.
9,579,039 B2 2/2017 Jansen et al.
9,583,236 B2 * 2/2017 Arzate ................. H01B 13/016
9,591,975 B2 3/2017 Dalvi et al.
9,622,692 B2 4/2017 Lamego et al.
9,622,693 B2 4/2017 Diab
D788,312 S 5/2017 Al-Ali et al.
9,636,055 B2 5/2017 Al Ali et al.
9,636,056 B2 5/2017 Al-Ali
9,649,054 B2 5/2017 Lamego et al.
9,662,052 B2 5/2017 Al-Ali et al.
9,668,679 B2 6/2017 Schurman et al.
9,668,680 B2 6/2017 Bruinsma et al.
9,668,703 B2 6/2017 Al-Ali
9,675,286 B2 6/2017 Diab
9,687,160 B2 6/2017 Kiani
9,693,719 B2 7/2017 Al-Ali et al.
9,693,737 B2 7/2017 Al-Ali
9,697,928 B2 7/2017 Al-Ali et al.
9,717,425 B2 8/2017 Kiani et al.
9,717,458 B2 8/2017 Lamego et al.
9,724,016 B1 8/2017 Al-Ali et al.
9,724,024 B2 8/2017 Al-Ali
9,724,025 B1 8/2017 Kiani et al.
9,743,887 B2 8/2017 Al-Ali et al.
9,749,232 B2 8/2017 Sampath et al.
9,750,442 B2 9/2017 Olsen
9,750,461 B1 9/2017 Telfort
9,775,545 B2 10/2017 Al-Ali et al.
9,775,546 B2 10/2017 Diab et al.
9,775,570 B2 10/2017 Al-Ali
9,778,079 B1 10/2017 Al-Ali et al.
9,782,077 B2 10/2017 Lamego et al.
9,782,110 B2 10/2017 Kiani
9,787,568 B2 10/2017 Lamego et al.
9,788,735 B2 10/2017 Al-Ali
9,788,768 B2 10/2017 Al-Ali et al.
9,795,300 B2 10/2017 Al-Ali
9,795,310 B2 10/2017 Al-Ali
9,795,358 B2 10/2017 Telfort et al.
9,795,739 B2 10/2017 Al-Ali et al.
9,801,556 B2 10/2017 Kiani
9,801,588 B2 10/2017 Weber et al.
9,808,188 B1 11/2017 Perea et al.
9,833,152 B2 12/2017 Kiani et al.
9,833,180 B2 12/2017 Shakespeare et al.
9,839,379 B2 12/2017 Al-Ali et al.
9,839,381 B1 12/2017 Weber et al.
9,847,749 B2 12/2017 Kiani et al.
9,848,800 B1 12/2017 Lee et al.
9,861,298 B2 1/2018 Eckerbom et al.
9,861,305 B1 1/2018 Weber et al.
9,877,650 B2 1/2018 Muhsin et al.
9,891,079 B2 2/2018 Dalvi
9,924,897 B1 3/2018 Abdul-Hafiz
9,936,917 B2 4/2018 Poeze et al.
9,955,937 B2 5/2018 Telfort
9,965,946 B2 5/2018 Al-Ali et al.
D820,865 S 6/2018 Muhsin et al.
9,986,952 B2 6/2018 Dalvi et al.
D822,215 S 7/2018 Al-Ali et al.
D822,216 S 7/2018 Barker et al.
10,010,276 B2 7/2018 Al-Ali et al.
10,086,138 B1 10/2018 Novak, Jr.
10,111,591 B2 10/2018 Dyell et al.
D833,624 S 11/2018 DeJong et al.
10,123,729 B2 11/2018 Dyell et al.
D835,282 S 12/2018 Barker et al.
D835,283 S 12/2018 Barker et al.
D835,284 S 12/2018 Barker et al.
D835,285 S 12/2018 Barker et al.
10,149,616 B2 12/2018 Al-Ali et al.
10,154,815 B2 12/2018 Al-Ali et al.
10,159,412 B2 12/2018 Lamego et al.
10,188,348 B2 1/2019 Al-Ali et al.
RE47,218 E 2/2019 Al-Ali
RE47,244 E 2/2019 Kiani et al.
RE47,249 E 2/2019 Kiani et al.
10,205,291 B2 2/2019 Scruggs et al.
10,226,187 B2 3/2019 Al-Ali et al.
10,231,657 B2 3/2019 Al-Ali et al.
10,231,670 B2 3/2019 Blank et al.
RE47,353 E 4/2019 Kiani et al.
10,279,247 B2 5/2019 Kiani
10,292,664 B2 5/2019 Al-Ali
10,299,720 B2 5/2019 Brown et al.
10,327,337 B2 6/2019 Schmidt et al.
10,327,713 B2 6/2019 Barker et al.
10,332,630 B2 6/2019 Al-Ali
10,383,520 B2 8/2019 Wojtczuk et al.
10,383,527 B2 8/2019 Al-Ali
10,388,120 B2 8/2019 Muhsin et al.
D864,120 S 10/2019 Forrest et al.
10,441,181 B1 10/2019 Telfort et al.
10,441,196 B2 10/2019 Eckerbom et al.
10,448,844 B2 10/2019 Al-Ali et al.
10,448,871 B2 10/2019 Al-Ali et al.
10,456,038 B2 10/2019 Lamego et al.
10,463,340 B2 11/2019 Telfort et al.
10,471,159 B1 11/2019 Lapotko et al.
10,505,311 B2 12/2019 Al-Ali et al.
10,524,738 B2 1/2020 Olsen
10,532,174 B2 1/2020 Al-Ali
10,537,285 B2 1/2020 Shreim et al.
10,542,903 B2 1/2020 Al-Ali et al.
10,555,678 B2 2/2020 Dalvi et al.
10,568,553 B2 2/2020 O'Neil et al.
RE47,882 E 3/2020 Al-Ali
10,608,817 B2 3/2020 Haider et al.
D880,477 S 4/2020 Forrest et al.
10,617,302 B2 4/2020 Al-Ali et al.
10,617,335 B2 4/2020 Al-Ali et al.
10,637,181 B2 4/2020 Al-Ali et al.
D886,849 S 6/2020 Muhsin et al.
D887,548 S 6/2020 Abdul-Hafiz et al.
D887,549 S 6/2020 Abdul-Hafiz et al.
10,667,764 B2 6/2020 Ahmed et al.
D890,708 S 7/2020 Forrest et al.
10,721,785 B2 7/2020 Al-Ali
10,736,518 B2 8/2020 Al-Ali et al.
10,750,984 B2 8/2020 Pauley et al.
D897,098 S 9/2020 Al-Ali
10,779,098 B2 9/2020 Iswanto et al.
10,827,961 B1 11/2020 Iyengar et al.
10,828,007 B1 11/2020 Telfort et al.
10,832,818 B2 11/2020 Muhsin et al.
10,849,554 B2 12/2020 Shreim et al.
10,856,750 B2 12/2020 Indorf
D906,970 S 1/2021 Forrest et al.
D908,213 S 1/2021 Abdul-Hafiz et al.
10,918,281 B2 2/2021 Al-Ali et al.
10,932,705 B2 3/2021 Muhsin et al.

(56) References Cited

U.S. PATENT DOCUMENTS 10,932,729 B2 3/2021 Kiani et al.
10,939,878 B2 3/2021 Kiani et al.
10,956,950 B2 3/2021 Al-Ali et al.
D916,135 S 4/2021 Indorf et al.
D917,046 S 4/2021 Abdul-Hafiz et al.
D917,550 S 4/2021 Indorf et al.
D917,564 S 4/2021 Indorf et al.
D917,704 S 4/2021 Al-Ali et al.
10,987,066 B2 4/2021 Chandran et al.
10,991,135 B2 4/2021 Al-Ali et al.
D919,094 S 5/2021 Al-Ali et al.
D919,100 S 5/2021 Al-Ali et al.
11,006,867 B2 5/2021 Al-Ali
D921,202 S 6/2021 Al-Ali et al.
11,024,064 B2 6/2021 Muhsin et al.
11,026,604 B2 6/2021 Chen et al.
D925,597 S 7/2021 Chandran et al.
11,069,461 B2 7/2021 Al-Ali et al.
D927,699 S 8/2021 Al-Ali et al.
11,076,777 B2 8/2021 Lee et al.
11,114,188 B2 9/2021 Poeze et al.
D933,232 S 10/2021 Al-Ali et al.
D933,233 S 10/2021 Al-Ali et al.
D933,234 S 10/2021 Al-Ali et al.
11,145,408 B2 10/2021 Sampath et al.
11,147,518 B1 10/2021 Al-Ali et al.
11,185,262 B2 11/2021 Al-Ali et al.
11,191,484 B2 12/2021 Kiani et al.
D946,596 S 3/2022 Ahmed
D946,597 S 3/2022 Ahmed
D946,598 S 3/2022 Ahmed
D946,617 S 3/2022 Ahmed
11,272,839 B2 3/2022 Al-Ali et al.
11,289,199 B2 3/2022 Al-Ali
RE49,034 E 4/2022 Al-Ali
11,298,021 B2 4/2022 Muhsin et al.
D950,580 S 5/2022 Ahmed
D950,599 S 5/2022 Ahmed
D950,738 S 5/2022 Al-Ali et al.
D957,648 S 7/2022 Al-Ali
11,382,567 B2 7/2022 O'Brien et al.
11,389,093 B2 7/2022 Triman et al.
11,406,286 B2 8/2022 Al-Ali et al.
11,417,426 B2 8/2022 Muhsin et al.
11,439,329 B2 9/2022 Lamego
11,445,948 B2 9/2022 Scruggs et al.
D965,789 S 10/2022 Al-Ali et al.
D967,433 S 10/2022 Al-Ali et al.
11,464,410 B2 10/2022 Muhsin
11,504,058 B1 11/2022 Sharma et al.
11,504,066 B1 11/2022 Dalvi et al.
D971,933 S 12/2022 Ahmed
D973,072 S 12/2022 Ahmed
D973,685 S 12/2022 Ahmed
D973,686 S 12/2022 Ahmed
D974,193 S 1/2023 Forrest et al.
11,557,407 B2 1/2023 Al-Ali et al.
D979,516 S 2/2023 Al-Ali et al.
D980,091 S 3/2023 Forrest et al.
11,596,363 B2 3/2023 Lamego
11,627,919 B2 4/2023 Kiani et al.
11,637,437 B2 4/2023 Al-Ali et al.
D985,498 S 5/2023 Al-Ali et al.
11,653,862 B2 5/2023 Dalvi et al.
D989,112 S 6/2023 Muhsin et al.
D989,327 S 6/2023 Al-Ali et al.
11,678,829 B2 6/2023 Al-Ali et al.
11,679,579 B2 6/2023 Al-Ali
11,684,296 B2 6/2023 Vo et al.
11,692,934 B2 7/2023 Normand et al.
11,701,043 B2 7/2023 Al-Ali et al.
D997,365 S 8/2023 Hwang
11,721,105 B2 8/2023 Ranasinghe et al.
11,730,379 B2 8/2023 Ahmed et al.
D998,625 S 9/2023 Indorf et al.
D998,630 S 9/2023 Indorf et al.
D998,631 S 9/2023 Indorf et al.
D999,244 S 9/2023 Indorf et al.
D999,245 S 9/2023 Indorf et al.
D999,246 S 9/2023 Indorf et al.
11,766,198 B2 9/2023 Pauley et al.
D1,000,975 S 10/2023 Al-Ali et al.
11,803,623 B2 10/2023 Kiani et al.
11,832,940 B2 12/2023 Diab et al.
D1,013,179 S 1/2024 Al-Ali et al.
11,872,156 B2 1/2024 Telfort et al.
11,879,960 B2 1/2024 Ranasinghe et al.
11,883,129 B2 1/2024 Olsen
D1,022,729 S 4/2024 Forrest et al.
11,951,186 B2 4/2024 Krishnamani et al.
11,974,833 B2 5/2024 Forrest et al.
11,986,067 B2 5/2024 Al-Ali et al.
11,986,289 B2 5/2024 Dalvi et al.
11,986,305 B2 5/2024 Al-Ali et al.
D1,031,729 S 6/2024 Forrest et al.
12,004,869 B2 6/2024 Kiani et al.
12,014,328 B2 6/2024 Wachman et al.
D1,036,293 S 7/2024 Al-Ali et al.
D1,037,462 S 7/2024 Al-Ali et al.
12,029,844 B2 7/2024 Pauley et al.
12,048,534 B2 7/2024 Vo et al.
12,064,217 B2 8/2024 Ahmed et al.
12,066,426 B1 8/2024 Lapotko et al.
D1,041,511 S 9/2024 Indorf et al.
D1,042,596 S 9/2024 DeJong et al.
D1,042,852 S 9/2024 Hwang
12,076,159 B2 9/2024 Belur Nagaraj et al.
12,082,926 B2 9/2024 Sharma et al.
D1,044,828 S 10/2024 Chandran et al.
D1,048,571 S 10/2024 Yu et al.
D1,048,908 S 10/2024 Al-Ali et al.
12,106,752 B2 10/2024 Campbell et al.
12,114,974 B2 10/2024 Al-Ali et al.
12,126,683 B2 10/2024 Koo et al.
12,127,838 B2 10/2024 Olsen et al.
12,128,213 B2 10/2024 Kiani et al.
12,131,661 B2 10/2024 Pauley et al.
D1,050,910 S 11/2024 Al-Ali et al.
12,178,572 B1 12/2024 Pauley et al.
12,178,581 B2 12/2024 Telfort et al.
12,178,852 B2 12/2024 Kiani et al.
D1,057,159 S 1/2025 DeJong et al.
D1,057,160 S 1/2025 DeJong et al.
12,198,790 B1 1/2025 Al-Ali
12,200,421 B2 1/2025 Campbell et al.
12,207,901 B1 1/2025 Lapotko et al.
D1,060,680 S 2/2025 Al-Ali et al.
D1,061,585 S 2/2025 Indorf
D1,063,893 S 2/2025 DeJong et al.
12,220,207 B2 2/2025 Telfort et al.
12,235,941 B2 2/2025 Kiani et al.
12,236,767 B2 2/2025 Muhsin
D1,066,244 S 3/2025 Lim et al.
D1,066,672 S 3/2025 Al-Ali et al.
D1,068,656 S 4/2025 Trevisan et al.
D1,071,195 S 4/2025 Seung
D1,072,836 S 4/2025 Indorf
D1,072,837 S 4/2025 Ahmed et al.
12,272,445 B1 4/2025 Kiani
D1,078,689 S 6/2025 Hwang
D1,079,020 S 6/2025 Hwang
12,336,796 B2 6/2025 Al-Ali
D1,083,653 S 7/2025 DeJong et al.
D1,085,102 S 7/2025 Indorf et al.
12,362,596 B2 7/2025 Barker et al.
12,390,114 B2 8/2025 Novak, Jr. et al.
D1,092,244 S 9/2025 DeJong et al.
D1,093,406 S 9/2025 Indorf et al.
D1,094,735 S 9/2025 DeJong et al.
D1,095,288 S 9/2025 Lim
D1,095,483 S 9/2025 DeJong et al.
12,433,524 B2 10/2025 Al-Ali et al.
12,440,128 B2 10/2025 Al-Ali et al.
D1,102,622 S 11/2025 Al-Ali et al.

(56) References Cited

U.S. PATENT DOCUMENTS 12,478,272 B2 11/2025 Telfort et al.
12,478,293 B1 11/2025 Al-Ali et al.
D1,106,466 S 12/2025 Avendaño et al.
12,495,967 B2 12/2025 Muhsin et al.
12,495,999 B2 12/2025 Al-Ali et al.
12,507,952 B2 12/2025 Al-Ali et al.
2001/0034477 A1 10/2001 Mansfield et al.
2001/0039483 A1 11/2001 Brand et al.
2002/0010401 A1 1/2002 Bushmakin et al.
2002/0058864 A1 5/2002 Mansfield et al.
2002/0095074 A1 7/2002 Ai-Ai
2002/0133080 A1 9/2002 Apruzzese et al.
2003/0013975 A1 1/2003 Kiani
2003/0018243 A1 1/2003 Gerhardt et al.
2003/0144582 A1 7/2003 Cohen et al.
2003/0156288 A1 8/2003 Barnum et al.
2003/0212312 A1 11/2003 Coffin, IV et al.
2004/0106163 A1 6/2004 Workman, Jr. et al.
2005/0055276 A1 3/2005 Kiani et al.
2005/0234317 A1 10/2005 Kiani
2006/0073719 A1 4/2006 Kiani
2006/0131059 A1* 6/2006 Xu ........................ H01B 3/427 174/117 F
2006/0189871 A1 8/2006 Al-Ali et al.
2007/0073116 A1 3/2007 Kiani et al.
2007/0180140 A1 8/2007 Welch et al.
2007/0244377 A1 10/2007 Cozad et al.
2007/0282478 A1 12/2007 Al-Ali et al.
2008/0064965 A1 3/2008 Jay et al.
2008/0094228 A1 4/2008 Welch et al.
2008/0103375 A1 5/2008 Kiani
2008/0221418 A1 9/2008 Al-Ali et al.
2009/0036759 A1 2/2009 Ault et al.
2009/0093687 A1 4/2009 Telfort et al.
2009/0095926 A1 4/2009 MacNeish, III
2009/0114418 A1 5/2009 Smith et al.
2009/0247984 A1 10/2009 Lamego et al.
2009/0275813 A1 11/2009 Davis
2009/0275844 A1 11/2009 Al-Ali
2010/0004518 A1 1/2010 Vo et al.
2010/0030040 A1 2/2010 Poeze et al.
2010/0099964 A1 4/2010 O'Reilly et al.
2010/0234718 A1 9/2010 Sampath et al.
2010/0270257 A1 10/2010 Wachman et al.
2010/0332689 A1 12/2010 Unuma et al.
2011/0001605 A1 1/2011 Kiani et al.
2011/0017491 A1 1/2011 Lu et al.
2011/0028806 A1 2/2011 Merritt et al.
2011/0028809 A1 2/2011 Goodman
2011/0040197 A1 2/2011 Welch et al.
2011/0082711 A1 4/2011 Poeze et al.
2011/0083877 A1* 4/2011 Sugiyama ............ H01B 7/0823 427/117
2011/0087081 A1 4/2011 Kiani et al.
2011/0105854 A1 5/2011 Kiani et al.
2011/0118561 A1 5/2011 Tari et al.
2011/0125060 A1 5/2011 Telfort et al.
2011/0137297 A1 6/2011 Kiani et al.
2011/0172498 A1 7/2011 Olsen et al.
2011/0208015 A1 8/2011 Welch et al.
2011/0213212 A1 9/2011 Ai-Ali
2011/0230733 A1 9/2011 Al-Ali
2011/0237911 A1 9/2011 Lamego et al.
2011/0237969 A1 9/2011 Eckerbom et al.
2011/0288383 A1 11/2011 Diab
2012/0041316 A1 2/2012 Al Ali et al.
2012/0046557 A1 2/2012 Kiani
2012/0059267 A1 3/2012 Lamego et al.
2012/0088984 A1 4/2012 Al-Ali et al.
2012/0123231 A1 5/2012 O'Reilly
2012/0165629 A1 6/2012 Merritt et al.
2012/0179006 A1 7/2012 Jansen et al.
2012/0209082 A1 8/2012 Al-Ali
2012/0209084 A1 8/2012 Olsen et al.
2012/0226117 A1 9/2012 Lamego et al.
2012/0227739 A1 9/2012 Kiani
2012/0283524 A1 11/2012 Kiani et al.
2012/0296178 A1 11/2012 Lamego et al.
2012/0319816 A1 12/2012 Al-Ali
2012/0330112 A1 12/2012 Lamego et al.
2013/0023775 A1 1/2013 Lamego et al.
2013/0041591 A1 2/2013 Lamego
2013/0046204 A1 2/2013 Lamego et al.
2013/0060147 A1 3/2013 Welch et al.
2013/0096405 A1 4/2013 Garfio
2013/0096936 A1 4/2013 Sampath et al.
2013/0190581 A1 7/2013 Al-Ali et al.
2013/0197328 A1 8/2013 Diab et al.
2013/0211214 A1 8/2013 Olsen
2013/0243021 A1 9/2013 Siskavich
2013/0253334 A1 9/2013 Al-Ali et al.
2013/0267804 A1 10/2013 Al-Ali
2013/0274572 A1 10/2013 Al-Ali et al.
2013/0296672 A1 11/2013 O'Neil et al.
2013/0296713 A1 11/2013 Al-Ali et al.
2013/0317370 A1 11/2013 Dalvi et al.
2013/0324808 A1 12/2013 Al-Ali et al.
2013/0331660 A1 12/2013 Al-Ali et al.
2013/0331670 A1 12/2013 Kiani
2013/0338461 A1 12/2013 Lamego et al.
2013/0345921 A1 12/2013 Al-Ali et al.
2014/0012100 A1 1/2014 Al-Ali et al.
2014/0051953 A1 2/2014 Lamego et al.
2014/0058230 A1 2/2014 Abdul-Hafiz et al.
2014/0066783 A1 3/2014 Kiani et al.
2014/0077956 A1 3/2014 Sampath et al.
2014/0081100 A1 3/2014 Muhsin et al.
2014/0081175 A1 3/2014 Telfort
2014/0094667 A1 4/2014 Schurman et al.
2014/0100434 A1 4/2014 Diab et al.
2014/0114199 A1 4/2014 Lamego et al.
2014/0120564 A1 5/2014 Workman et al.
2014/0121482 A1 5/2014 Merritt et al.
2014/0121483 A1 5/2014 Kiani
2014/0127137 A1 5/2014 Bellott et al.
2014/0129702 A1 5/2014 Lamego et al.
2014/0135588 A1 5/2014 Al-Ali et al.
2014/0142401 A1 5/2014 Al-Ali et al.
2014/0163344 A1 6/2014 Al-Ali
2014/0163402 A1 6/2014 Lamego et al.
2014/0166076 A1 6/2014 Kiani et al.
2014/0171763 A1 6/2014 Diab
2014/0180038 A1 6/2014 Kiani
2014/0180154 A1 6/2014 Sierra et al.
2014/0180160 A1 6/2014 Brown et al.
2014/0187973 A1 7/2014 Brown et al.
2014/0194709 A1 7/2014 Al-Ali et al.
2014/0194711 A1 7/2014 Al-Ali
2014/0194766 A1 7/2014 Al-Ali et al.
2014/0206963 A1 7/2014 Al-Ali
2014/0213864 A1 7/2014 Abdul-Hafiz et al.
2014/0243627 A1 8/2014 Diab et al.
2014/0266790 A1 9/2014 Al-Ali et al.
2014/0275808 A1 9/2014 Poeze et al.
2014/0275835 A1 9/2014 Lamego et al.
2014/0275871 A1 9/2014 Lamego et al.
2014/0275872 A1 9/2014 Merritt et al.
2014/0275881 A1 9/2014 Lamego et al.
2014/0276115 A1 9/2014 Dalvi et al.
2014/0288400 A1 9/2014 Diab et al.
2014/0303520 A1 10/2014 Telfort et al.
2014/0316217 A1 10/2014 Purdon et al.
2014/0316218 A1 10/2014 Purdon et al.
2014/0316228 A1 10/2014 Blank et al.
2014/0323825 A1 10/2014 Al-Ali et al.
2014/0323897 A1 10/2014 Brown et al.
2014/0323898 A1 10/2014 Purdon et al.
2014/0330092 A1 11/2014 Al-Ali et al.
2014/0330098 A1 11/2014 Merritt et al.
2014/0330099 A1 11/2014 Al-Ali et al.
2014/0333440 A1 11/2014 Kiani
2014/0336481 A1 11/2014 Shakespeare et al.
2014/0343436 A1 11/2014 Kiani
2014/0357966 A1 12/2014 Al-Ali et al.

(56) References Cited

U.S. PATENT DOCUMENTS

2015/0005600 A1 1/2015 Blank et al.
2015/0011907 A1 1/2015 Purdon et al.
2015/0012231 A1 1/2015 Poeze et al.
2015/0018650 A1 1/2015 Al-Ali et al.
2015/0025406 A1 1/2015 Al-Ali
2015/0032029 A1 1/2015 Al-Ali et al.
2015/0038859 A1 2/2015 Dalvi et al.
2015/0045637 A1 2/2015 Dalvi
2015/0051462 A1 2/2015 Olsen
2015/0073241 A1 3/2015 Lamego
2015/0080754 A1 3/2015 Purdon et al.
2015/0087936 A1 3/2015 Al-Ali et al.
2015/0094546 A1 4/2015 Al-Ali
2015/0097701 A1 4/2015 Muhsin et al.
2015/0099950 A1 4/2015 Al-Ali et al.
2015/0099951 A1 4/2015 Al-Ali et al.
2015/0099955 A1 4/2015 Al-Ali et al.
2015/0101844 A1 4/2015 Al-Ali et al.
2015/0106121 A1 4/2015 Muhsin et al.
2015/0112151 A1 4/2015 Muhsin et al.
2015/0116076 A1 4/2015 Al-Ali et al.
2015/0126830 A1 5/2015 Schurman et al.
2015/0133755 A1 5/2015 Smith et al.
2015/0141781 A1 5/2015 Weber et al.
2015/0165312 A1 6/2015 Kiani
2015/0196237 A1 7/2015 Lamego
2015/0216459 A1 8/2015 Al-Ali et al.
2015/0224641 A1 8/2015 Herring et al.
2015/0230755 A1 8/2015 Al-Ali et al.
2015/0238722 A1 8/2015 Al-Ali
2015/0245773 A1 9/2015 Lamego et al.
2015/0245794 A1 9/2015 Al-Ali
2015/0257689 A1 9/2015 Al-Ali et al.
2015/0272514 A1 10/2015 Kiani et al.
2015/0351697 A1 12/2015 Weber et al.
2015/0351704 A1 12/2015 Kiani et al.
2015/0359429 A1 12/2015 Al-Ali et al.
2015/0366472 A1 12/2015 Kiani
2015/0366507 A1 12/2015 Blank et al.
2015/0374298 A1 12/2015 Al-Ali et al.
2015/0380875 A1 12/2015 Coverston et al.
2016/0000362 A1 1/2016 Diab et al.
2016/0007930 A1 1/2016 Weber et al.
2016/0029932 A1 2/2016 Al-Ali
2016/0045118 A1 2/2016 Kiani
2016/0051205 A1 2/2016 Al-Ali et al.
2016/0058338 A1 3/2016 Schurman et al.
2016/0058347 A1 3/2016 Reichgott et al.
2016/0066823 A1 3/2016 Al-Ali et al.
2016/0066824 A1 3/2016 Al-Ali et al.
2016/0066879 A1 3/2016 Telfort et al.
2016/0072429 A1 3/2016 Kiani et al.
2016/0081552 A1 3/2016 Wojtczuk et al.
2016/0095543 A1 4/2016 Telfort et al.
2016/0095548 A1 4/2016 Al-Ali et al.
2016/0103598 A1 4/2016 Al-Ali et al.
2016/0113527 A1 4/2016 Al-Ali
2016/0143548 A1 5/2016 Al-Ali
2016/0166182 A1 6/2016 Al-Ali et al.
2016/0166183 A1 6/2016 Poeze et al.
2016/0166188 A1 6/2016 Bruinsma et al.
2016/0166210 A1 6/2016 Ai-Ai
2016/0192869 A1 7/2016 Kiani et al.
2016/0196388 A1 7/2016 Lamego
2016/0197436 A1 7/2016 Barker et al.
2016/0213281 A1 7/2016 Eckerbom et al.
2016/0228043 A1 8/2016 O'Neil et al.
2016/0233632 A1 8/2016 Scruggs et al.
2016/0234944 A1 8/2016 Schmidt et al.
2016/0270735 A1 9/2016 Diab et al.
2016/0283665 A1 9/2016 Sampath et al.
2016/0287090 A1 10/2016 Al-Ali et al.
2016/0287786 A1 10/2016 Kiani
2016/0296169 A1 10/2016 McHale et al.
2016/0310052 A1 10/2016 Al-Ali et al.
2016/0314260 A1 10/2016 Kiani
2016/0324486 A1 11/2016 Al-Ali et al.
2016/0324488 A1 11/2016 Olsen
2016/0327984 A1 11/2016 Al-Ali et al.
2016/0328528 A1 11/2016 Al-Ali et al.
2016/0331332 A1 11/2016 Al-Ali
2016/0367173 A1 12/2016 Dalvi et al.
2017/0007134 A1 1/2017 Al-Ali et al.
2017/0007190 A1 1/2017 Al-Ali et al.
2017/0007198 A1 1/2017 Al-Ali et al.
2017/0014084 A1 1/2017 Al-Ali et al.
2017/0021099 A1 1/2017 Al-Ali et al.
2017/0024748 A1 1/2017 Haider
2017/0027456 A1 2/2017 Kinast et al.
2017/0042488 A1 2/2017 Muhsin
2017/0055847 A1 3/2017 Kiani et al.
2017/0055851 A1 3/2017 Al-Ali
2017/0055882 A1 3/2017 Al-Ali et al.
2017/0055887 A1 3/2017 Al-Ali
2017/0055896 A1 3/2017 Al-Ali
2017/0079594 A1 3/2017 Telfort et al.
2017/0086723 A1 3/2017 Al-Ali et al.
2017/0143281 A1 5/2017 Olsen
2017/0147774 A1 5/2017 Kiani
2017/0156620 A1 6/2017 Al-Ali et al.
2017/0173632 A1 6/2017 Al-Ali
2017/0187146 A1 6/2017 Kiani et al.
2017/0188919 A1 7/2017 Al-Ali et al.
2017/0196464 A1 7/2017 Jansen et al.
2017/0196470 A1 7/2017 Lamego et al.
2017/0202490 A1 7/2017 Al-Ali et al.
2017/0224216 A1 8/2017 Al-Ali
2017/0224231 A1 8/2017 Al-Ali
2017/0224233 A1 8/2017 Al-Ali
2017/0224262 A1 8/2017 Al-Ali
2017/0231537 A1 8/2017 Al-Ali
2017/0245790 A1 8/2017 Al-Ali et al.
2017/0251974 A1 9/2017 Shreim et al.
2017/0251975 A1 9/2017 Shreim et al.
2017/0258403 A1 9/2017 Abdul-Hafiz et al.
2017/0311891 A1 11/2017 Kiani et al.
2018/0103874 A1 4/2018 Lee et al.
2018/0242926 A1 8/2018 Muhsin et al.
2018/0247353 A1 8/2018 Al-Ali et al.
2018/0247712 A1 8/2018 Muhsin et al.
2018/0256087 A1 9/2018 Al-Ali et al.
2018/0300919 A1 10/2018 Muhsin et al.
2018/0310822 A1 11/2018 Indorf et al.
2018/0310823 A1 11/2018 Al-Ali et al.
2018/0317826 A1 11/2018 Muhsin et al.
2019/0015023 A1 1/2019 Monfre
2019/0117070 A1 4/2019 Muhsin et al.
2019/0200941 A1 7/2019 Chandran et al.
2019/0239787 A1 8/2019 Pauley et al.
2019/0320906 A1 10/2019 Olsen
2019/0374139 A1 12/2019 Kiani et al.
2019/0374173 A1 12/2019 Kiani et al.
2019/0374713 A1 12/2019 Kiani et al.
2020/0060869 A1 2/2020 Telfort et al.
2020/0111552 A1 4/2020 Ahmed
2020/0113435 A1 4/2020 Muhsin
2020/0113488 A1 4/2020 Al-Ali et al.
2020/0113496 A1 4/2020 Scruggs et al.
2020/0113497 A1 4/2020 Triman et al.
2020/0113520 A1 4/2020 Abdul-Hafiz et al.
2020/0138288 A1 5/2020 Al-Ali et al.
2020/0138368 A1 5/2020 Kiani et al.
2020/0163597 A1 5/2020 Dalvi et al.
2020/0196877 A1 6/2020 Vo et al.
2020/0253474 A1 8/2020 Muhsin et al.
2020/0253544 A1 8/2020 Belur Nagaraj et al.
2020/0275841 A1 9/2020 Telfort et al.
2020/0288983 A1 9/2020 Telfort et al.
2020/0321793 A1 10/2020 Al-Ali et al.
2020/0329983 A1 10/2020 Al-Ali et al.
2020/0329984 A1 10/2020 Al-Ali et al.
2020/0329993 A1 10/2020 Al-Ali et al.
2020/0330037 A1 10/2020 Al-Ali et al.
2021/0022628 A1 1/2021 Telfort et al.

(56) References Cited

U.S. PATENT DOCUMENTS

| | | | |
|---|---|---|---|
| 2021/0104173 | A1 | 4/2021 | Pauley et al. |
| 2021/0113121 | A1 | 4/2021 | Diab et al. |
| 2021/0117525 | A1 | 4/2021 | Kiani et al. |
| 2021/0118581 | A1 | 4/2021 | Kiani et al. |
| 2021/0121582 | A1 | 4/2021 | Krishnamani et al. |
| 2021/0161465 | A1 | 6/2021 | Barker et al. |
| 2021/0236729 | A1 | 8/2021 | Kiani et al. |
| 2021/0256267 | A1 | 8/2021 | Ranasinghe et al. |
| 2021/0256835 | A1 | 8/2021 | Ranasinghe et al. |
| 2021/0275101 | A1 | 9/2021 | Vo et al. |
| 2021/0290060 | A1 | 9/2021 | Ahmed |
| 2021/0290072 | A1 | 9/2021 | Forrest |
| 2021/0290080 | A1 | 9/2021 | Ahmed |
| 2021/0290120 | A1 | 9/2021 | Al-Ali |
| 2021/0290177 | A1 | 9/2021 | Novak, Jr. |
| 2021/0290184 | A1 | 9/2021 | Ahmed |
| 2021/0296008 | A1 | 9/2021 | Novak, Jr. |
| 2021/0330228 | A1 | 10/2021 | Olsen et al. |
| 2021/0386382 | A1 | 12/2021 | Olsen et al. |
| 2021/0402110 | A1 | 12/2021 | Pauley et al. |
| 2022/0026355 | A1 | 1/2022 | Normand et al. |
| 2022/0039707 | A1 | 2/2022 | Sharma et al. |
| 2022/0053892 | A1 | 2/2022 | Al-Ali et al. |
| 2022/0071562 | A1 | 3/2022 | Kiani |
| 2022/0096603 | A1 | 3/2022 | Kiani et al. |
| 2022/0151521 | A1 | 5/2022 | Krishnamani et al. |
| 2022/0218244 | A1 | 7/2022 | Kiani et al. |
| 2022/0287574 | A1 | 9/2022 | Telfort et al. |
| 2022/0296161 | A1 | 9/2022 | Al-Ali et al. |
| 2022/0361819 | A1 | 11/2022 | Al-Ali et al. |
| 2022/0379059 | A1 | 12/2022 | Yu et al. |
| 2022/0392610 | A1 | 12/2022 | Kiani et al. |
| 2023/0028745 | A1 | 1/2023 | Al-Ali |
| 2023/0038389 | A1 | 2/2023 | Vo |
| 2023/0045647 | A1 | 2/2023 | Vo |
| 2023/0058052 | A1 | 2/2023 | Ai-Ai |
| 2023/0058342 | A1 | 2/2023 | Kiani |
| 2023/0069789 | A1 | 3/2023 | Koo et al. |
| 2023/0087671 | A1 | 3/2023 | Telfort et al. |
| 2023/0110152 | A1 | 4/2023 | Forrest et al. |
| 2023/0111198 | A1 | 4/2023 | Yu et al. |
| 2023/0115397 | A1 | 4/2023 | Vo et al. |
| 2023/0116371 | A1 | 4/2023 | Mills et al. |
| 2023/0135297 | A1 | 5/2023 | Kiani et al. |
| 2023/0138098 | A1 | 5/2023 | Telfort et al. |
| 2023/0145155 | A1 | 5/2023 | Krishnamani et al. |
| 2023/0147750 | A1 | 5/2023 | Barker et al. |
| 2023/0210417 | A1 | 7/2023 | Al-Ali et al. |
| 2023/0222805 | A1 | 7/2023 | Muhsin et al. |
| 2023/0222887 | A1 | 7/2023 | Muhsin et al. |
| 2023/0226331 | A1 | 7/2023 | Kiani et al. |
| 2023/0284916 | A1 | 9/2023 | Telfort |
| 2023/0284943 | A1 | 9/2023 | Scruggs et al. |
| 2023/0301562 | A1 | 9/2023 | Scruggs et al. |
| 2023/0346993 | A1 | 11/2023 | Kiani et al. |
| 2023/0368221 | A1 | 11/2023 | Haider |
| 2023/0371893 | A1 | 11/2023 | Al-Ali et al. |
| 2023/0389837 | A1 | 12/2023 | Krishnamani et al. |
| 2024/0016418 | A1 | 1/2024 | Devadoss et al. |
| 2024/0016419 | A1 | 1/2024 | Devadoss et al. |
| 2024/0047061 | A1 | 2/2024 | Al-Ali et al. |
| 2024/0049310 | A1 | 2/2024 | Al-Ali et al. |
| 2024/0049986 | A1 | 2/2024 | Al-Ali et al. |
| 2024/0081656 | A1 | 3/2024 | DeJong et al. |
| 2024/0122486 | A1 | 4/2024 | Kiani |
| 2024/0180456 | A1 | 6/2024 | Al-Ali |
| 2024/0188872 | A1 | 6/2024 | Al-Ali et al. |
| 2024/0245855 | A1 | 7/2024 | Vo et al. |
| 2024/0260894 | A1 | 8/2024 | Olsen |
| 2024/0267698 | A1 | 8/2024 | Telfort et al. |
| 2024/0277233 | A1 | 8/2024 | Al-Ali |
| 2024/0277280 | A1 | 8/2024 | Ai-Ali |
| 2024/0298920 | A1 | 9/2024 | Fernkbist et al. |
| 2024/0306985 | A1 | 9/2024 | Vo et al. |
| 2024/0324953 | A1 | 10/2024 | Telfort |
| 2024/0380246 | A1 | 11/2024 | Moran |
| 2024/0380247 | A1 | 11/2024 | Moran |
| 2024/0404549 | A1 | 12/2024 | Campbell et al. |
| 2025/0000458 | A1 | 1/2025 | Abdul-Hafiz et al. |
| 2025/0037836 | A1 | 1/2025 | Kiani |
| 2025/0100482 | A1 | 3/2025 | Al-Ali et al. |
| 2025/0118415 | A1 | 4/2025 | Olsen |
| 2025/0255764 | A1 | 8/2025 | Stead |
| 2025/0278512 | A1 | 9/2025 | Koo et al. |
| 2025/0281059 | A1 | 9/2025 | Avendano |
| 2025/0288250 | A1 | 9/2025 | Al-Ali et al. |
| 2025/0295366 | A1 | 9/2025 | Al-Ali et al. |
| 2025/0302426 | A1 | 10/2025 | Ha et al. |
| 2025/0311949 | A1 | 10/2025 | Al-Ali et al. |
| 2025/0318761 | A1 | 10/2025 | Al-Ali et al. |
| 2025/0322950 | A1 | 10/2025 | Al-Ali et al. |
| 2025/0323417 | A1 | 10/2025 | Rey |
| 2025/0329240 | A1 | 10/2025 | Kiani |
| 2025/0344010 | A1 | 11/2025 | Al-Ali et al. |

OTHER PUBLICATIONS

US 2022/0192529 A1, 06/2022, Al-Ali et al. (withdrawn)
US 2024/0016391 A1, 01/2024, Lapotko et al. (withdrawn)
Extended European Search Report for Application No. 13178619.6 dated Nov. 22, 2013 in 8 pages.

* cited by examiner 300
301

310
312
320
322
330
340
350
360

400
500
710
720
720
730
730
700

400
560
A
A
720
500
730
700

400
322
330
312
560
320
310
710
700
DETAIL A-A

AUTOMATED ASSEMBLY SENSOR CABLE

PRIORITY CLAIM TO RELATED PROVISIONAL APPLICATIONS

The present application is a continuation of U.S. patent application Ser. No. 17/354,117, filed Jun. 22, 2021, titled Automated Assembly Sensor Cable, which is a continuation of U.S. patent application Ser. No. 15/637,835, filed Jun. 29, 2017, titled Automated Assembly Sensor Cable, which is a continuation of U.S. patent application Ser. No. 13/951,313, filed Jul. 25, 2013, titled Automated Assembly Sensor Cable, which claims priority benefit under 35 U.S.C. § 119(e) to U.S. Provisional Patent Application Ser. No. 61/678,107, filed Aug. 1, 2012, titled Automated Assembly Sensor Cable, hereby incorporated in its entirety by reference herein.

BACKGROUND OF THE INVENTION

Pulse oximetry is a widely accepted noninvasive procedure for measuring the oxygen saturation level of arterial blood, an indicator of a person's oxygen supply. A typical pulse oximetry system utilizes an optical sensor clipped onto a fingertip to measure the relative volume of oxygenated hemoglobin in pulsatile arterial blood flowing within the fingertip. Oxygen saturation ($SpO_2$), pulse rate and a plethysmograph waveform, which is a visualization of pulsatile blood flow over time, are displayed on a monitor accordingly.

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, California and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. patent application Ser. No. 11/367,036, filed Mar. 1, 2006, titled Configurable Physiological Measurement System; U.S. patent application Ser. No. 11/367,034, filed Mar. 1, 2006, titled Physiological Parameter Confidence Measure and U.S. patent application Ser. No. 11/366,208, filed Mar. 1, 2006, titled Noninvasive Multi-Parameter Patient Monitor, all assigned to Cercacor Laboratories, Irvine, CA (Cercacor) and all incorporated by reference herein. Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Such advanced pulse oximeters, low noise sensors and advanced blood parameter systems have gained rapid acceptance in a wide variety of medical applications, including surgical wards, intensive care and neonatal units, general wards, home care, physical training, and virtually all types of monitoring scenarios.

SUMMARY OF THE INVENTION

FIGS. 1A-B illustrate a typical pulse oximetry sensor 100 having a body 110, a cable 120 and a connector 130. The body 110 is configured to wrap around a fingertip and incorporates an emitter 140 and detector 150 that provide physiological measurements responsive to a patient's blood oxygen saturation, as described above. The body 110 incorporates a cable assembly 101, an emitter assembly 102, a shielded detector assembly 103 and a tape layer assembly 104. The cable 120 provides electrical communication between the connector 130, the emitter 140 and the detector 150. The connector 130 electrically and mechanically connects the sensor 100 to a monitor (not shown). In particular, the cable 120 has a pair of emitter conductors 121 that solder to emitter 140 leads and a pair of detector conductors 122 that solder to detector 150 leads. This electrical/mechanical attachment of cable leads to emitter and detector leads does not lend itself to automation, as described with respect to FIGS. 2A-B, below.

FIGS. 2A-B illustrate a typical pulse oximetry sensor cable 200, such as the cable 120 (FIGS. 1A-B) described with respect to FIGS. 1A-B, above. In particular, a pair of emitter wires 220 and a shielded twisted pair of detector wires 230 is encased in an elongated cylindrical jacket 210. Disadvantageously, this cable arrangement does not readily lend itself to an automated assembly process. This is due, in part, to the lack of an external cable feature that identifies the location of internal emitter 220 and detector 230 wires. Advantageously, an automated assembly sensor cable supports an automated assembly of optical sensors, as described with respect to FIGS. 3-4.

One aspect of an automated assembly sensor cable is a generally wide and flat elongated body and a registration feature generally traversing the length of the body so as to identify the relative locations of conductors within the body for ease of automated attachment of optical sensor components and sensor connectors to opposite ends of the sensor cable. In various embodiments, the automated assembly sensor cable has a conductor set of insulated wires, a conductive inner jacket generally surrounding the conductor set, a conductive drain line embedded within the inner jacket, a strength member embedded within the inner jacket, an outer jacket generally surrounding the inner jacket and a registration feature disposed along the surface of the outer jacket.

In various other embodiments, the conductor set and conductive drain line are linearly arranged and regular spaced so as readily land on a corresponding series of flexible circuit (flex circuit) or printed circuit board (PCB) conductors. The registration feature is a machine-readable groove or, alternatively, a printed line running the length of the sensor cable. The outer jacket and inner jacket are semi-pressure co-extruded PVC. The outer jacket incorporates Kevlar fibers for strength and the strength member is a high-strength cord of Kevlar strands. The regular spacing of the conductor set and conductive drain line is 0.050 inches. The conductor set has a pair of emitter wires for transmitting drive currents to sensor LEDs and a pair of detector wires for receiving currents from sensor photodiodes. In other embodiments, the registration feature is any of various mechanical, electrical, magnetic, electro-mechanical, electro-magnetic or optical features incorporated within or on the sensor cable so as to aid in cable orientation and alignment to pads or other conductor terminations on any of various flexible circuits, printed circuit boards, ceramic substrates or other carriers, boards, circuits or substrates for any of various electrical, optical or mechanical components.

Another aspect of a sensor cable automated assembly cable is a generally wide and flat elongated cable having a plurality of linearly-aligned, regularly-spaced conductors. The cable is cut to a length compatible with an optical sensing application. At least one end of the cable is prepared so as to expose the conductors. A registration feature disposed along the length of the cable is detected so as to indicate the relative to the location of at least a particular one of the conductors within the cable. The exposed conductors are positioned relative to sensor circuit contacts according to the registration feature. The conductors are attached to the contacts so as to provide electrical communications between the conductors and a plurality of optical components.

In various embodiments, the cable is prepared by identifying an outer jacket and an inner jacket of the cable. Portions of the outer jacket and the inner jacket are cut from around the conductors. Insulation is removed from the conductor ends and the conductor ends are tinned. In an embodiment, the registration feature is detected by mechanically sensing a groove disposed along the length of the cable. Alternatively, the registration feature is detected by optically sensing a printed line disposed along the length of the cable. The exposed conductors are located relative to optical sensor flexible circuit pads according to the registration feature. In an embodiment, the conductors are located by aligning a detector pair of conductors and an emitter pair of conductors with corresponding pairs of the pads. These conductors are then soldered or otherwise electrically and mechanically attached to the pads. In an embodiment, the emitter conductor pair and the detector conductor pair have color-coded insulation so as to aid visual verification of the automated sensor cable assembly. In an embodiment, the emitter conductor pair are orange and red and the detector conductor pair are green and white.

A further aspect of an automated assembly sensor cable is a generally wide and flat elongated body. A conductor set means is disposed within the body for transmitting drive currents to sensor LEDs and for receiving currents from sensor photodiodes. A registration means indentifies the relative locations of the conductor set means so as to automate attachment of connectors and circuitry. An inner jacket means mechanically surrounds and electrically shields the conductor set. A conductive means is embedded within the inner jacket for draining electrical charge from the body. A strength means is embedded within the inner jacket for adding strength to the body. An outer jacket means encloses and protects the body by generally surrounding the inner jacket means.

DETAILED DESCRIPTION OF THE PREFERRED EMBODIMENTS

Figures 1A, 1B:
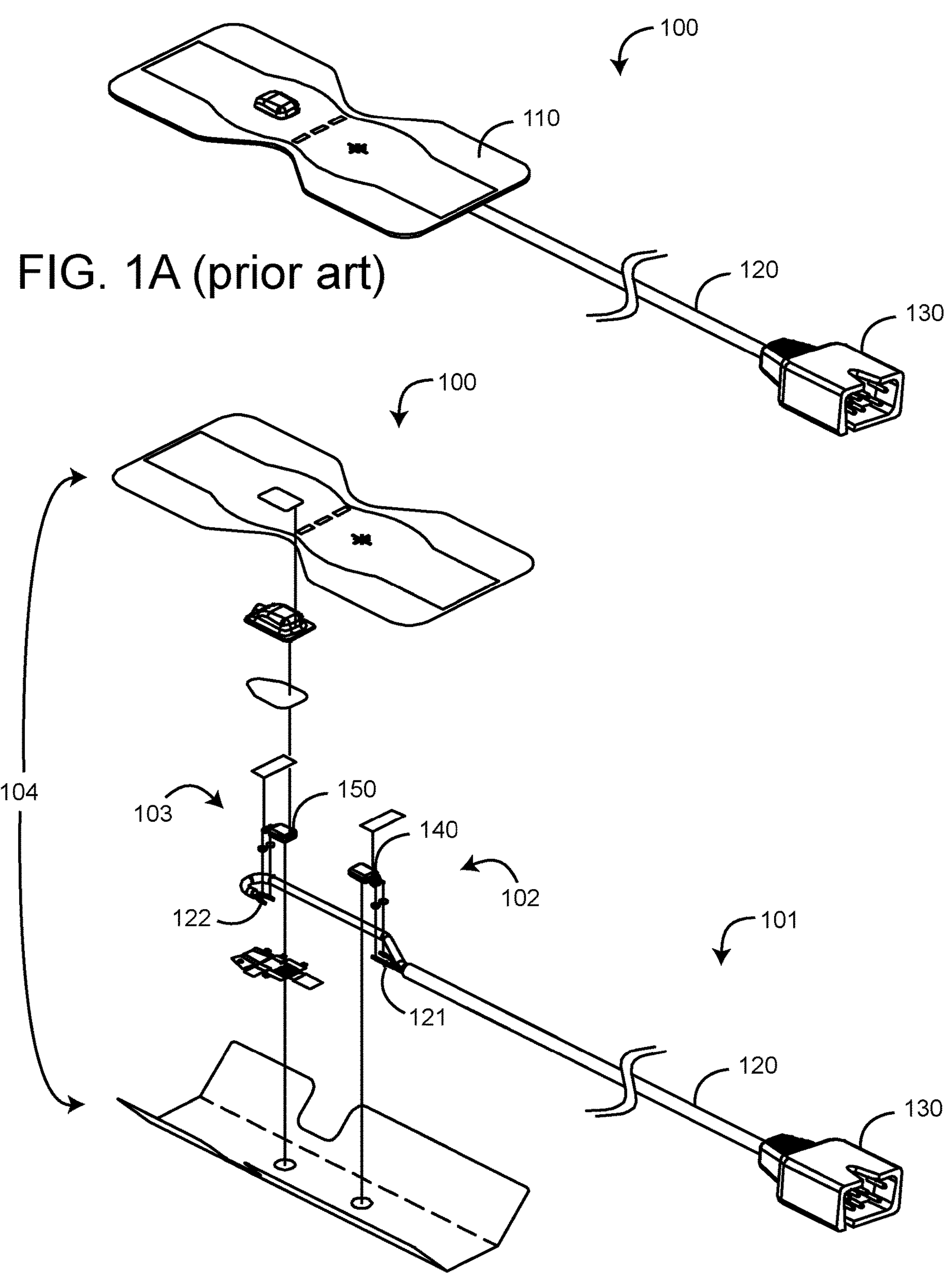
FIGS. 1A-B are assembled and exploded views, respectively, of a prior art pulse oximetry sensor.
Figure 2B:
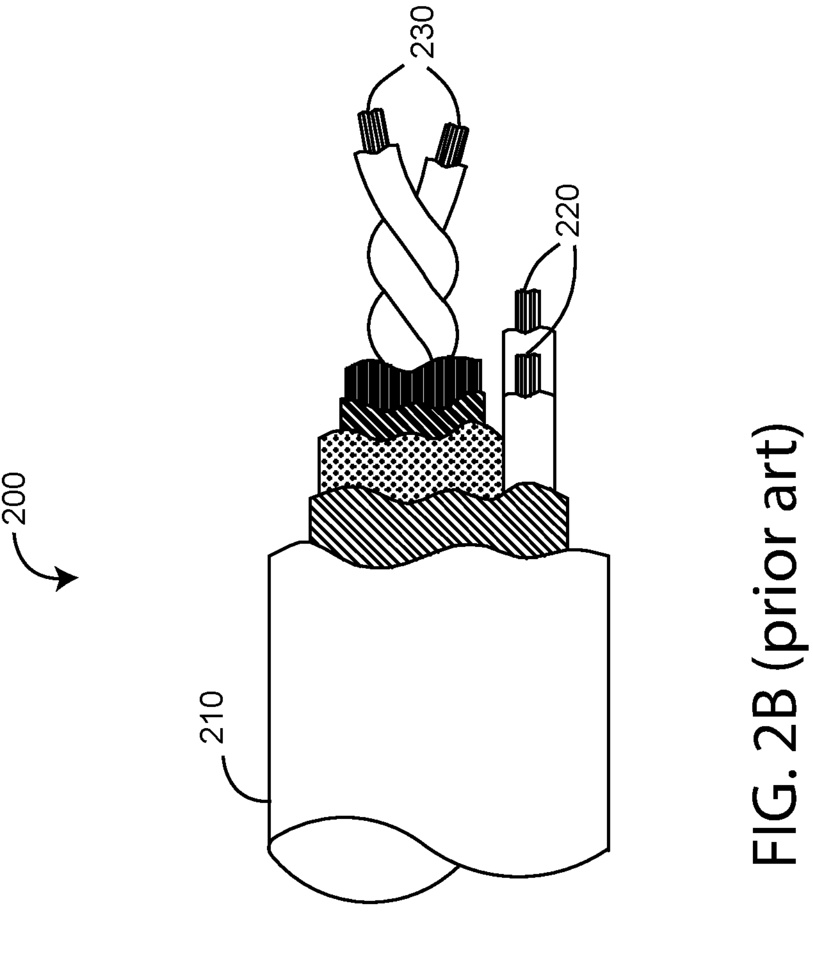
FIGS. 2A-B are cross-section and side cutaway views, respectively, of a prior art pulse oximetry sensor cable.
Figure 2A:
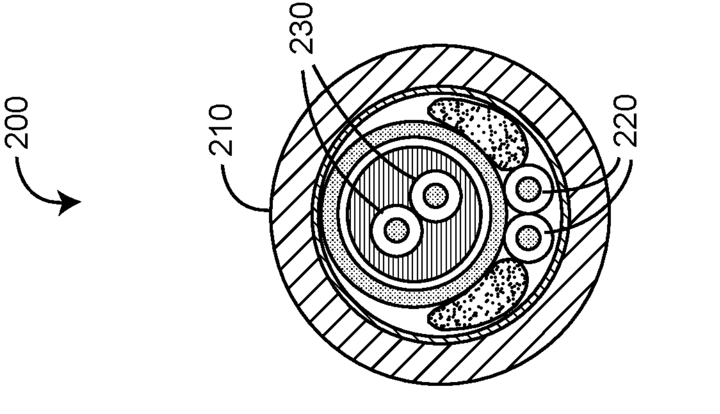

FIGS. 3A-G illustrate an automated assembly sensor cable 300 embodiment having a relatively flat and wide body 301 with linearly-arranged conductors sets 310, 320 and a machine-readable registration feature 360 so as to facilitate automatic location and attachment of specific conductors to specific connector pins or pads, as described with respect to FIGS. 4-6, below. In a particular embodiment, the sensor cable has a PVC semi-pressure extruded outer jacket 350 and a co-extruded conductive PVC inner jacket 340. The inner jacket 340 surrounds the conductor sets 310, 320 and an embedded drain line 330. The inner jacket 340 acts as a conductor shield, replacing conventional braided wire shielding. In an embodiment, Kevlar fibers are added to the outer jacket 350 for strength. In an embodiment, the registration feature 360 is a centralized groove formed in the surface of the outer layer during extrusion. In another embodiment, the registration feature is a printed line on the outer jacket 350 surface. In an embodiment, the conductors 310, 320 and the drain line 330 are linearly arranged and regularly spaced so as to facilitate automated assembly. In an embodiment, the conductor and drain line spacing is 0.050 inches. In an embodiment, the conductors 310, 320 are a copper core disposed within polypropylene insulation 312, 322.

Figures 4A, 4B:
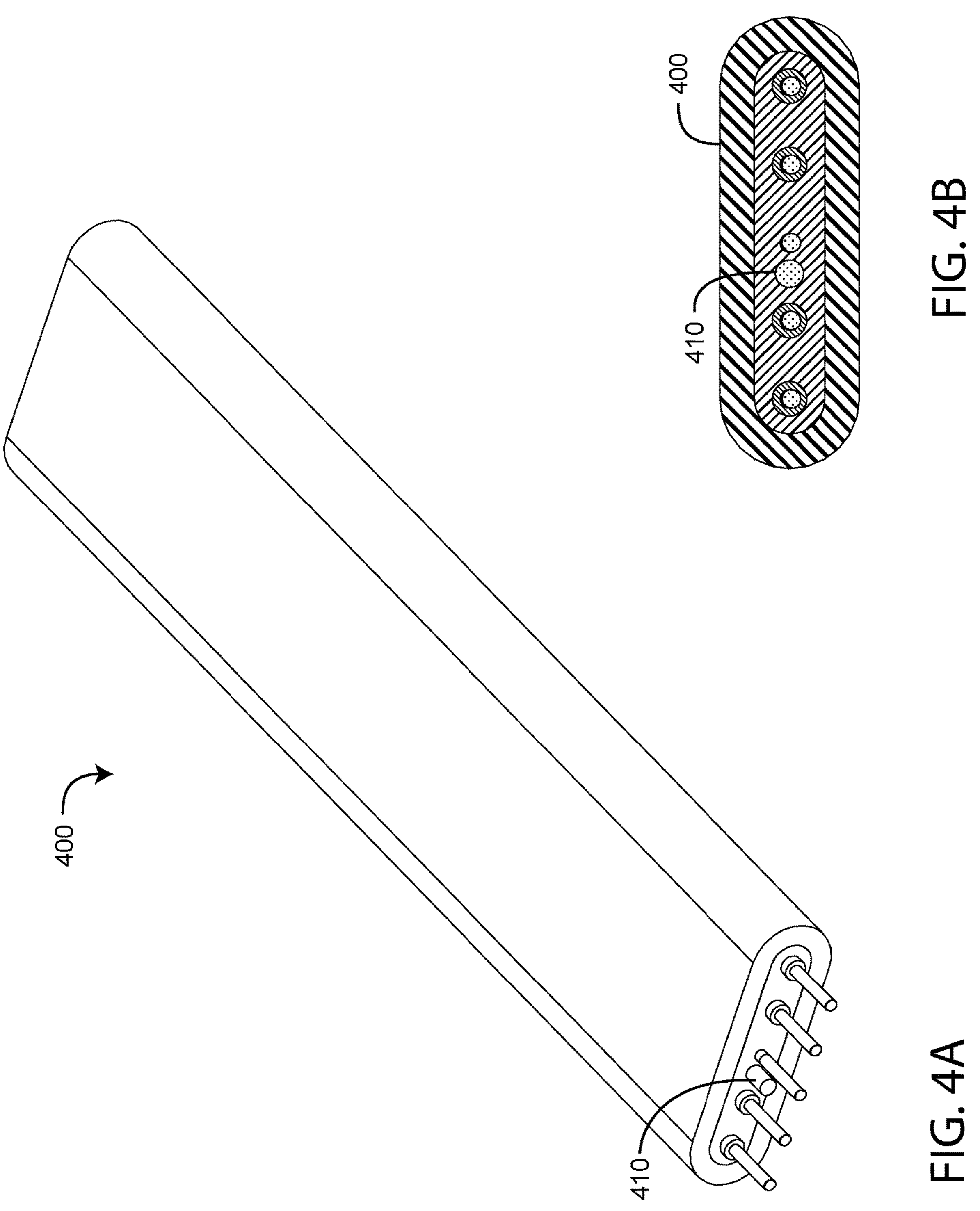
FIGS. 4A-B are top perspective and enlarged end views, respectively, of another automated assembly sensor cable embodiment having an embedded strength member.

FIGS. 4A-B illustrate another automated assembly sensor cable 400 embodiment having an embedded strength member 410 molded into the cable. Advantageously, the strength member transfers the considerable manufacturing-process cable loads off of the sensor cable conductors. In an embodiment, the strength member is a high-strength cord of Kevlar strands or the like.

Figures 5A, 5B, 5C:
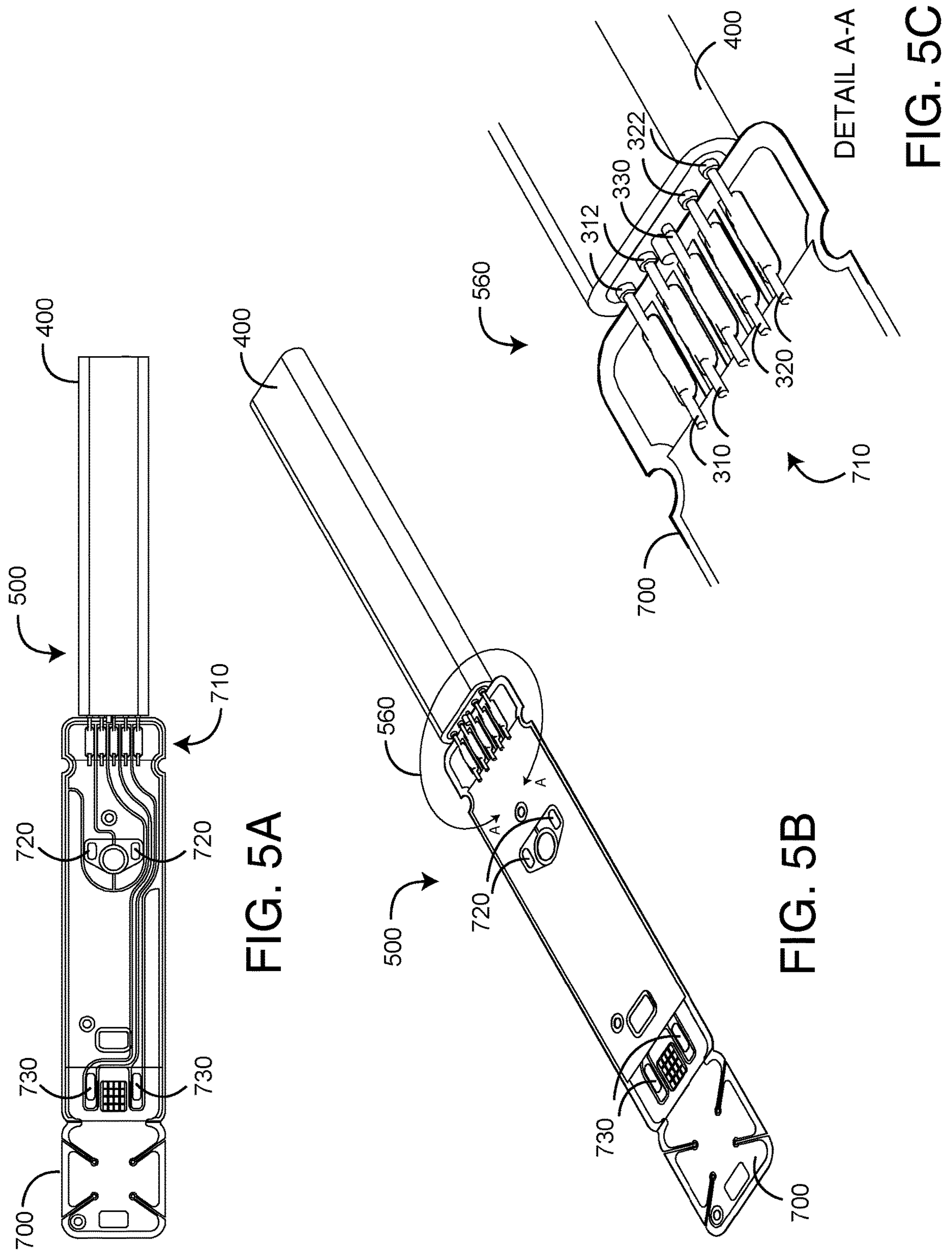
FIGS. 5A-C are top, top perspective and detailed top perspective views, respectively, of an automated assembly sensor cable soldered to a sensor flex circuit.

FIGS. 5A-C illustrate a sensor circuit assembly 500 having an automated assembly sensor cable 400 soldered to a sensor flex circuit 700. The regular spacing of the cable conductors 310-330 along an axis across the sensor cable 400 advantageously allows the cable to easily land on a series of pads 710 on a flex circuit 700 or PCB. In an embodiment, the cable conductor insulation is color coded for ease of visual identification and placement verification. In an embodiment, one of the emitter conductors 310 is coded orange and the other is coded red, and one of the detector conductors 320 is coded white and the other is coded green.

Figures 3A, 3B, 3C, 3D, 3E, 3F, 3G:
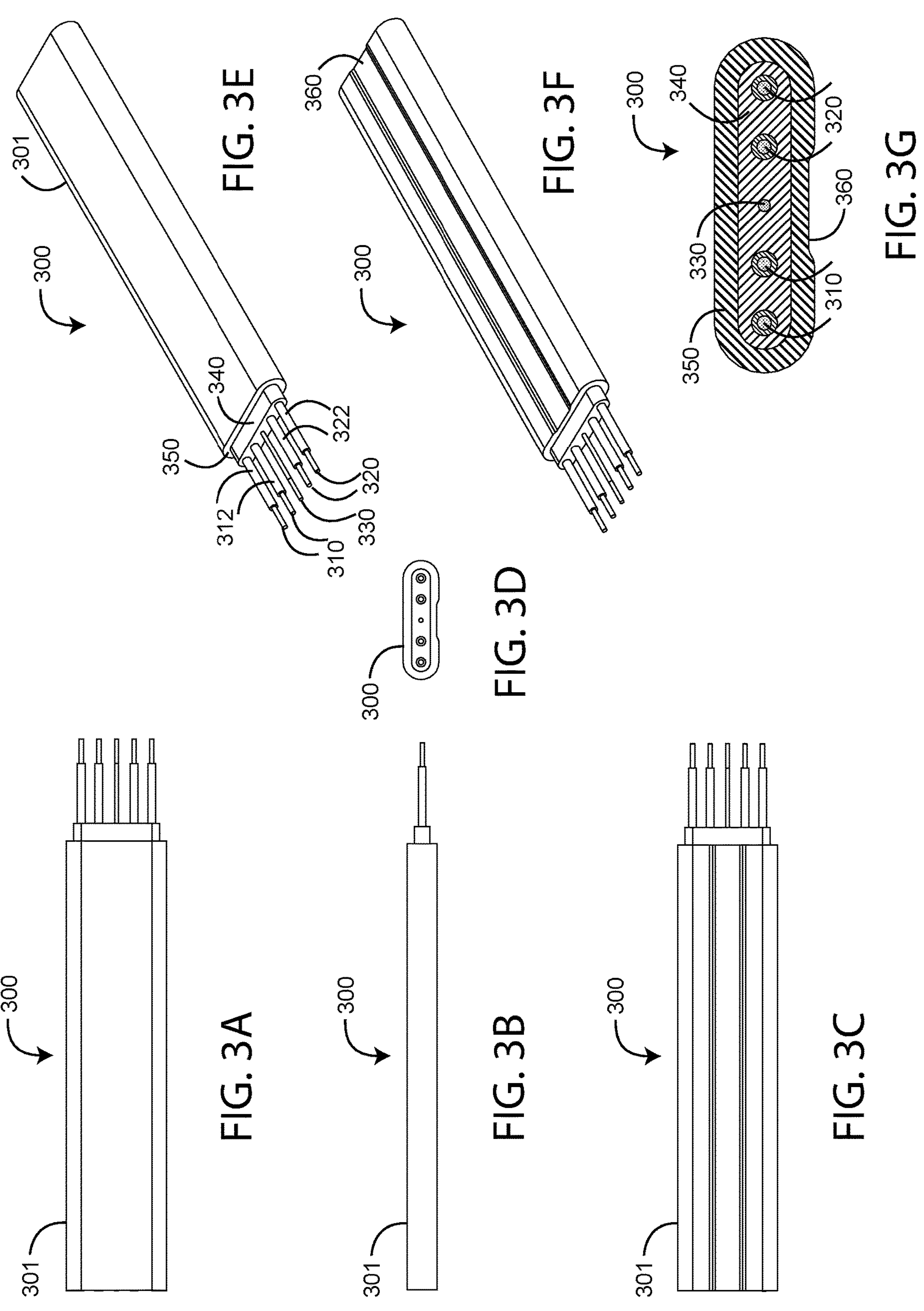
FIGS. 3A-G are top, side, bottom, end, top perspective, bottom perspective and enlarged end views, respectively, of an automated assembly sensor cable embodiment.
Figure 6:
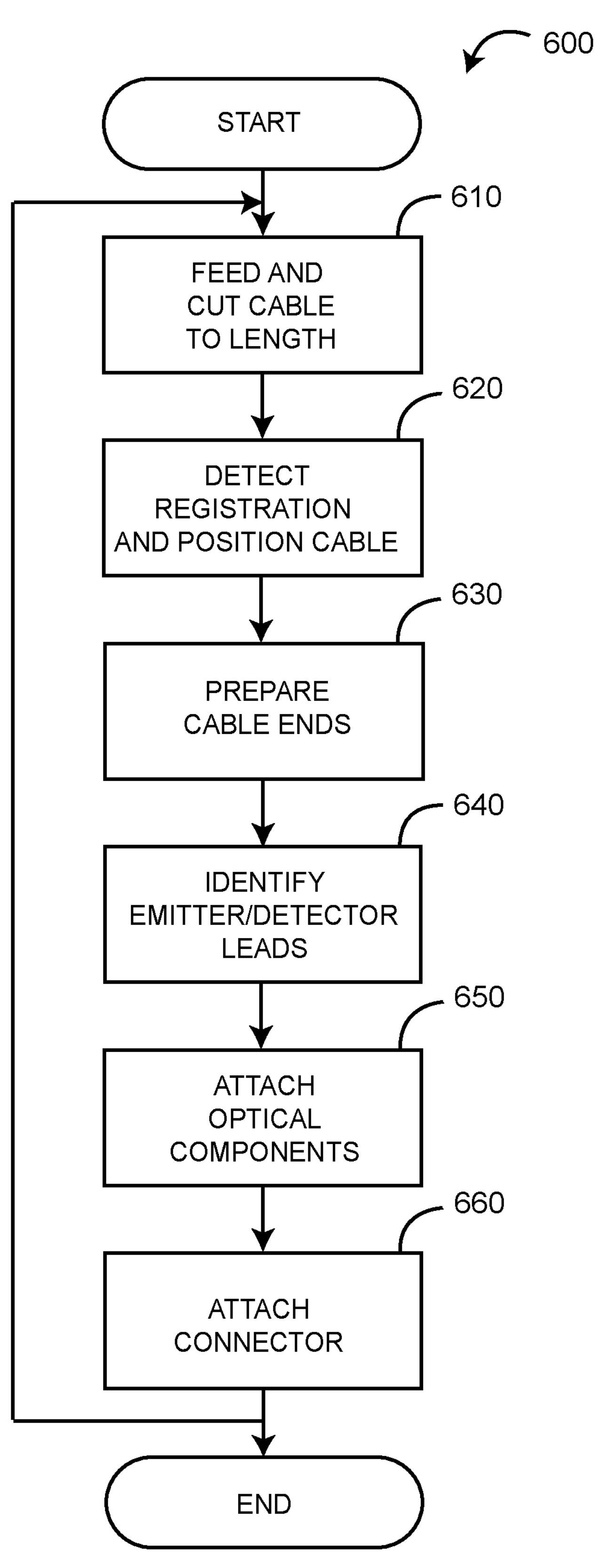
FIG. 6 is a generalized sensor manufacturing flowchart incorporating an automated assembly sensor cable.

FIG. 6 illustrates a sensor manufacturing method 600 utilizing an automated assembly sensor cable 300-400 (FIGS. 3-4). In an embodiment, sensor manufacturing starts with a roll of sensor cable or similar contiguous cable supply. A section of the sensor cable suitable for a particular use is measured and cut to length 610. The cable ends are prepared 620 by trimming predetermined lengths of the outer jacket 350 (FIG. 3G), the inner jacket 340 (FIG. 3G) and the various conductors 310-330 (FIG. 3G). Further, conductor insulation is stripped to length and conductors are pre-tinned accordingly. The registration feature 360 (FIG. 3F-G) is detected and the cable is positioned over flex circuit pads 710 (FIG. 5C) of a sensor flex circuit or PCB accordingly 630. The sensor circuit 700 (FIGS. 5A-C) is then soldered or otherwise mechanically and electrically attached to the sensor cable 400 (FIGS. 5A-C) leads 640. The opposite end of the sensor cable is similarly cut, trimmed and soldered so as to attach a sensor connector 650. The process is repeated for each sensor cable. In an embodiment, proper attachment of the sensor cable to the sensor circuit is visually verified 660 by the color coded emitter 312 and detector 322 (FIG. 5C) insulation.

An automated assembly sensor cable has been disclosed in detail in connection with various embodiments. These embodiments are disclosed by way of examples only and are not to limit the scope of the disclosure herein. One of ordinary skill in art will appreciate many variations and modifications.

What is claimed is:

1. A sensor cable comprising:

a conductor set of insulated wires, each of the insulated wires in the sensor cable comprising a conductive core disposed within an insulation layer;

a drain line;

an inner jacket extending immediately around the insulation layer of each of the insulated wires in the sensor cable and the drain line, the inner jacket having flat surfaces on at least two elongated sides of the inner jacket; and an outer jacket extending around the inner jacket, the outer jacket having a flat outer surface on at least two elongate sides of the outer jacket, wherein one of the at least two elongated sides of the outer jacket has no more than one groove formed on its flat outer surface, the no more than one groove extending along an entire length of the outer jacket and along a center of the flat outer surface on the one of the at least two elongated sides of the outer jacket, the no more than one groove comprises a flat bottom and two walls, the two walls having planar sections that are slanted relative to the flat bottom, wherein at least two wires of the conductor set are positioned between the flat outer surfaces on opposite sides of the inner jacket; and a flex circuit comprising a plurality of pads configured to electrically connect to a sensor, the plurality of pads comprising at least three pads that are linearly arranged and regularly spaced, the conductor set and the drain line being soldered at first ends to the plurality of pads.

2. The sensor cable of claim 1, in combination with the sensor, the sensor being electrically connected to the plurality of pads and comprising an emitter configured to emit light and a detector configured to detect the light after attenuation by tissue.

3. The sensor cable of claim 1, in combination with the sensor, the sensor being electrically connected to the plurality of pads and comprising an emitter configured to emit light and a detector configured to detect the light after attenuation by tissue, the sensor being configured to wrap around a fingertip of a user.

4. The sensor cable of claim 1, in combination with the sensor, the sensor being electrically connected to the plurality of pads and configured to receive a control signal from a first wire of the conductor set and transmit a data signal to a second wire of the conductor set via the plurality of pads, the control signal being configured to control an operation of the sensor, the data signal comprising sensor data generated by the sensor.

5. The sensor cable of claim 1, wherein the conductor set includes a total of at least four wires.

6. The sensor cable of claim 1, wherein the conductor set and the drain line are configured to electrically connect to a patient monitor at second ends of the conductor set and the drain line opposite to the first ends.

7. The sensor cable of claim 1, wherein the drain line is configured to drain electrical charge from the inner jacket.

8. The sensor cable of claim 1, wherein the drain line is not surrounded by a wire insulation like the wire insulation that generally surrounds each wire of the conductor set.

9. The sensor cable of claim 1, wherein wire insulations of the conductor set are color coded to separately visually identify individual wires of the conductor set from one another.

10. The sensor cable of claim 1, wherein a first wire of the conductor set and a second wire of the conductor set are positioned within the inner jacket at a common distance from the no more than one groove.

11. The sensor cable of claim 1, wherein the inner jacket and the outer jacket comprise PVC.

12. The sensor cable of claim 11, wherein the inner jacket comprises co-extruded conductive PVC, and the outer jacket comprises semi-pressure extruded PVC.

13. The sensor cable of claim 11, wherein the inner jacket is conductive.

14. The sensor cable of claim 1, wherein the conductor set and the drain line are electrically connected to the plurality of pads on a common side of the flex circuit.

15. The sensor cable of claim 1, wherein the plurality of pads comprise at least four pads that are linearly arranged and regularly spaced.

16. The sensor cable of claim 1, wherein the two walls are symmetrical relative to the flat bottom.

17. The sensor cable of claim 1, wherein the plurality of pads are electrically connected to the sensor.

* * * * *